United States Patent
Hagiwara

(10) Patent No.: US 11,884,905 B2
(45) Date of Patent: Jan. 30, 2024

(54) FLUIDIC CHIP FOR CELL CULTURE USE, CULTURE VESSEL, AND CULTURE METHOD

(71) Applicant: University Public Corporation Osaka, Osaka (JP)

(72) Inventor: Masaya Hagiwara, Sakai (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 1111 days.

(21) Appl. No.: 16/484,506

(22) PCT Filed: Jan. 18, 2018

(86) PCT No.: PCT/JP2018/001402
§ 371 (c)(1),
(2) Date: Aug. 8, 2019

(87) PCT Pub. No.: WO2018/147032
PCT Pub. Date: Aug. 16, 2018

(65) Prior Publication Data
US 2020/0032186 A1    Jan. 30, 2020

(30) Foreign Application Priority Data

Feb. 9, 2017  (JP) ................................. 2017-022223
Aug. 22, 2017  (JP) ................................. 2017-159658

(51) Int. Cl.
| C12M 3/06 | (2006.01) |
| C12M 1/00 | (2006.01) |
| C12M 1/12 | (2006.01) |
| C12N 5/071 | (2010.01) |

(52) U.S. Cl.
CPC ............ *C12M 23/16* (2013.01); *C12M 23/22* (2013.01); *C12M 23/34* (2013.01); *C12M 23/38* (2013.01); *C12M 25/14* (2013.01); *C12N 5/0602* (2013.01)

(58) Field of Classification Search
CPC ...... C12M 23/16; C12M 23/22; C12M 23/34; C12M 23/38; C12M 25/14; C12M 21/08; C12M 25/16; C12N 5/0602; C12N 5/00; G01N 37/00
See application file for complete search history.

(56) References Cited

U.S. PATENT DOCUMENTS

| 10,988,723 B1 * | 4/2021 | Hatch .................... C12M 23/46 |
| 2003/0082795 A1 | 5/2003 | Shuler et al. |
| 2008/0233607 A1 | 9/2008 | Yu et al. |
| 2011/0159522 A1 * | 6/2011 | Kamm ............... G01N 33/5029 435/287.1 |
| 2014/0057311 A1 * | 2/2014 | Kamm ................... C12M 25/14 216/33 |
| 2016/0145555 A1 | 5/2016 | Ingber et al. |
| 2016/0282338 A1 | 9/2016 | Miklas et al. |
| 2019/0076840 A1 * | 3/2019 | Gottardi ............ B01L 3/502715 |
| 2022/0169970 A1 * | 6/2022 | Hagiwara .............. C12M 23/16 |

FOREIGN PATENT DOCUMENTS

| JP | 2005-503169 A | 2/2005 |
| JP | 2008-519598 A | 6/2008 |
| JP | 2014-113118 A | 6/2014 |
| JP | 2016-533184 A | 10/2016 |
| WO | 2009/126524 A1 | 10/2009 |
| WO | 2012/050981 A1 | 4/2012 |

OTHER PUBLICATIONS

Huang et al, Egg-in-Cube: Design and Fabrication of a Novel Artificial Eggshell with Functionalized Surface. PLoS One Mar. 13, 2015.*
Huang et al (Egg-in-Cube: Design and Fabrication of a Novel Artificial Eggshell with Functionalized Surface. PLoS One, vol. 10, Mar. 2015) (Year: 2015).*
Hamer at al (An Improved Method for Measurement of Gel Strength and Data on Starch Gels. Part of the Journal of Research of the National Bureau of Standards. vol. 39, Jul. 1947) (Year: 1947).*
Caliari et al (A practical guide to hydrogels for cell culture. Nature Methods, vol. 13, May 2016) (Year: 2016).*

(Continued)

*Primary Examiner* — Kara D Johnson
*Assistant Examiner* — Matasha Dhar
(74) *Attorney, Agent, or Firm* — Stites & Harbison, PLLC; Jeffrey A. Haeberlin; Patrick M. Torre

(57) ABSTRACT

The present invention provides a fluidic chip for cell culture use which can prevent a decrease in the activity of cultured cells in a preparation stage, and which makes it possible to observe a cultured cell tissue while detaching the cultured cell tissue from the fluidic chip. The fluidic chip according to the present invention is characterized by being provided with a base and a lid member, wherein the base and the lid member are configured in such a manner that a first flow path and a first accommodation section for attachably/detachably accommodating a first culture vessel are formed between the base and the lid member when the base and the lid member are bonded to each other, the first culture vessel encloses a culture gel into which cells or a cell tissue is to be embedded and is at least partially formed from a hydrogel or a porous body, and the base and the lid member are configured in such a manner that at least a portion of a culture solution flowing through the first flow path is supplied to the first accommodation section.

11 Claims, 9 Drawing Sheets

(56) References Cited

OTHER PUBLICATIONS

Lee et al (Hydrogel-Based Three-Dimensional Cell Culture for Organ-on-a-Chip Applications. Biotechnology Progress, Mar. 2017) (Year: 2017).*

Hagiwara, M., et al. "Tissue in Cube: In Vitro 3D Culturing Platform with Hybrid Gel Cubes for Multidirectional Observations," Adv. Healthcare Mater., 2016, vol. 5, pp. 1566-1571. (See: ISR).

Japan Patent Office, International Search Report issued in corresponding Application No. PCT/JP2018/001402, dated Apr. 24, 2018.

European Patent Office, Extended European Search Report issued in corresponding Application No. 18751504.4 dated Dec. 4, 2020.

* cited by examiner

[Fig. 1]
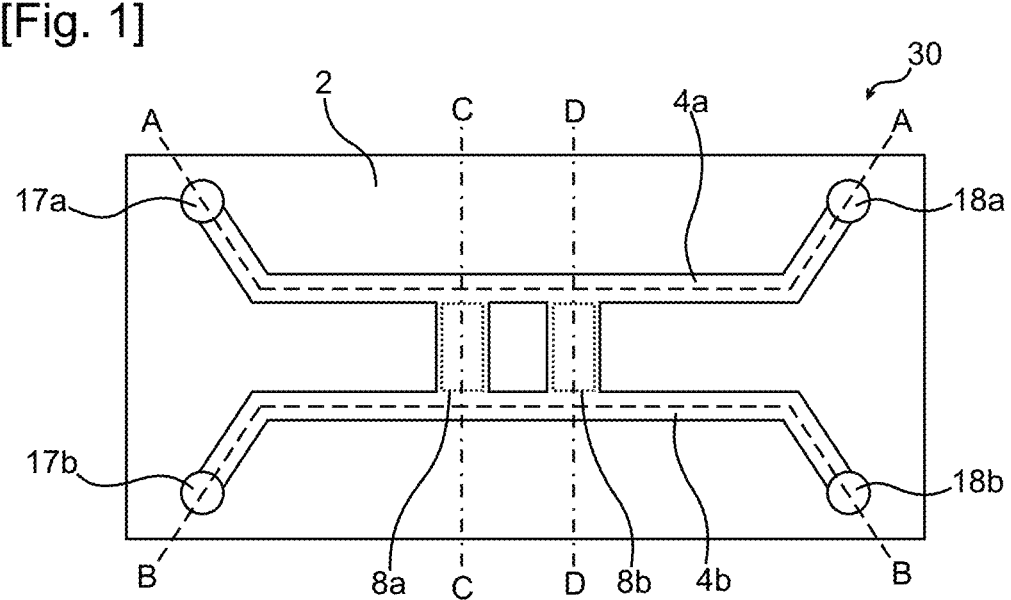
[Fig. 2]
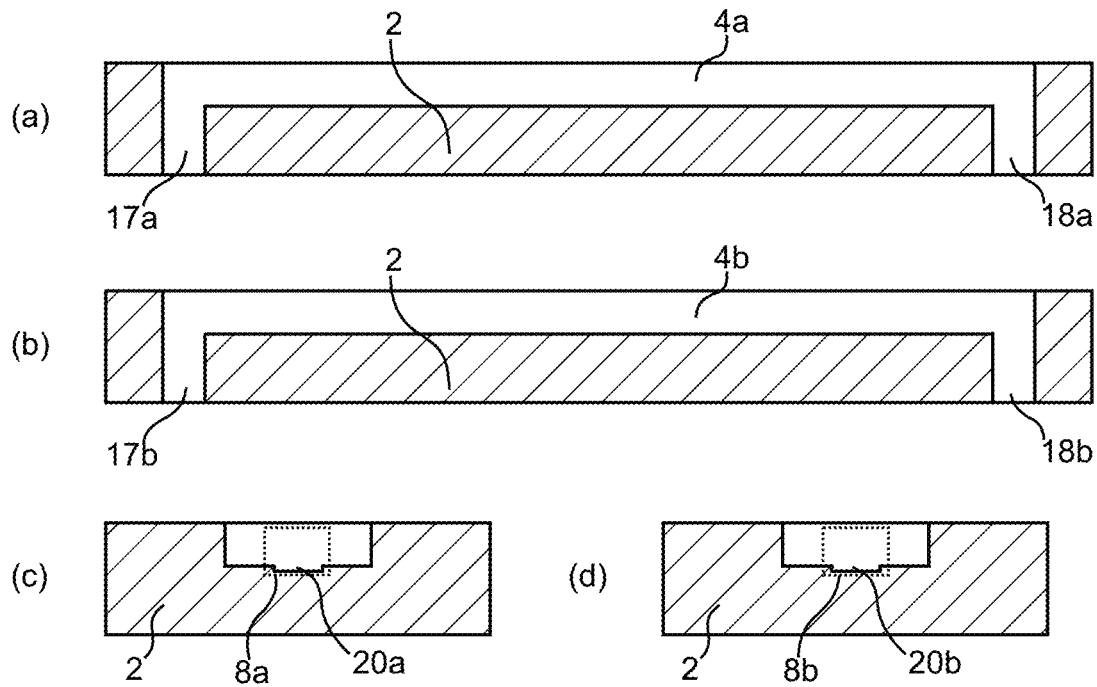

[Fig. 3]
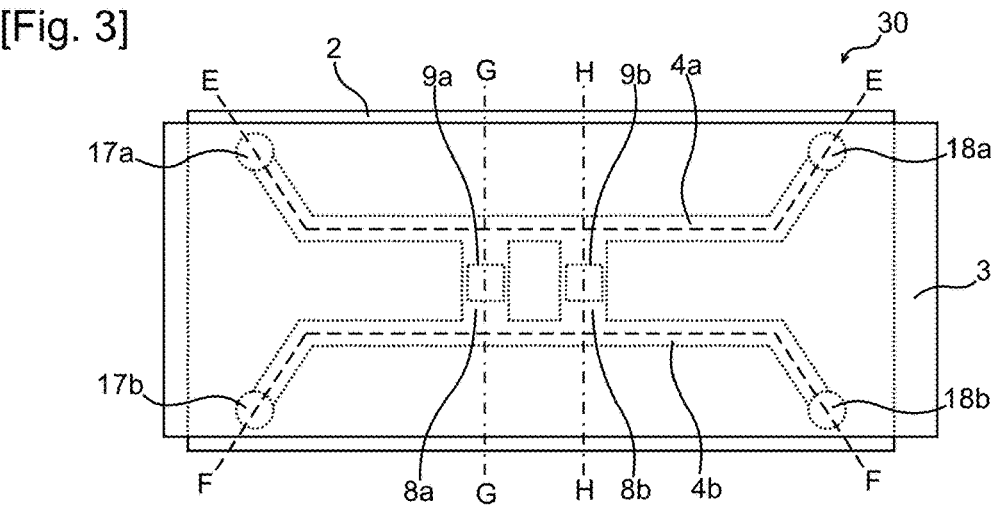
[Fig. 4]
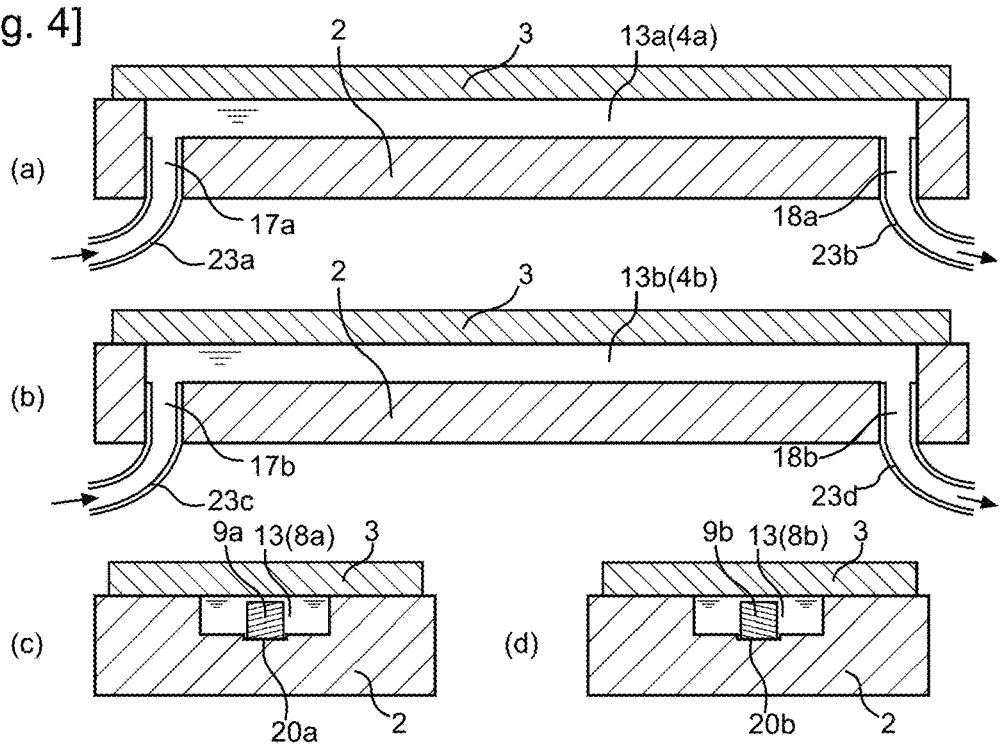
[Fig. 5]
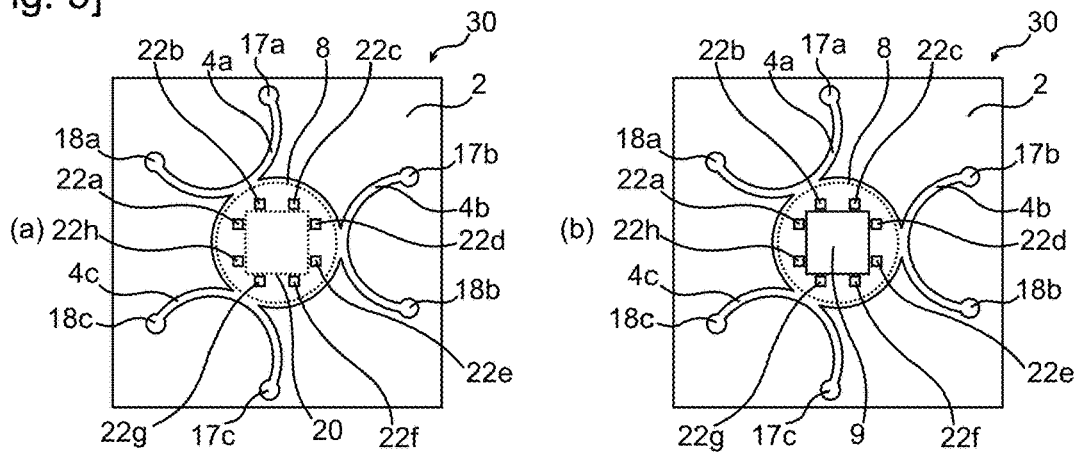

[Fig. 6]
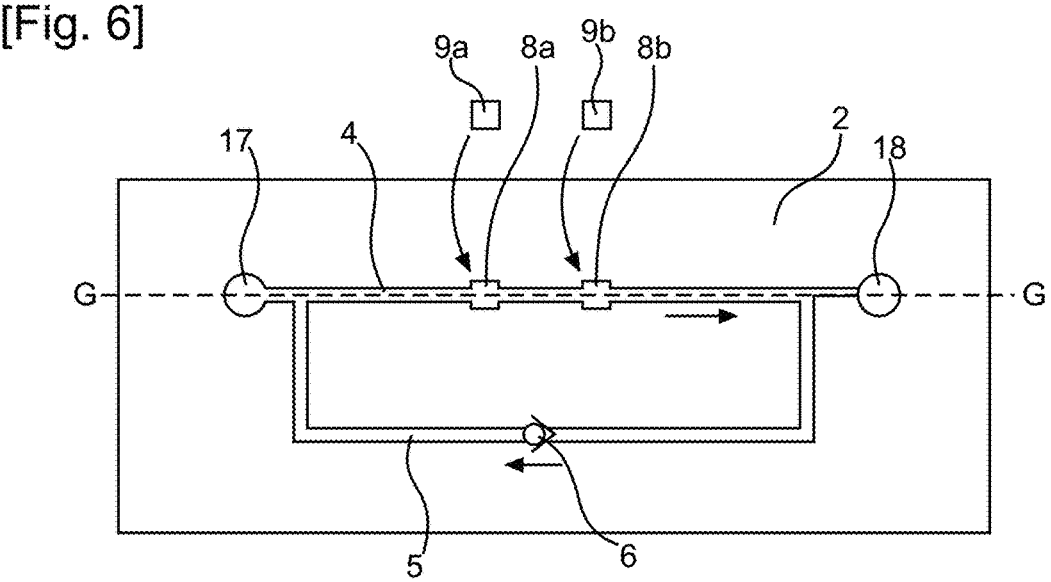
[Fig. 7]
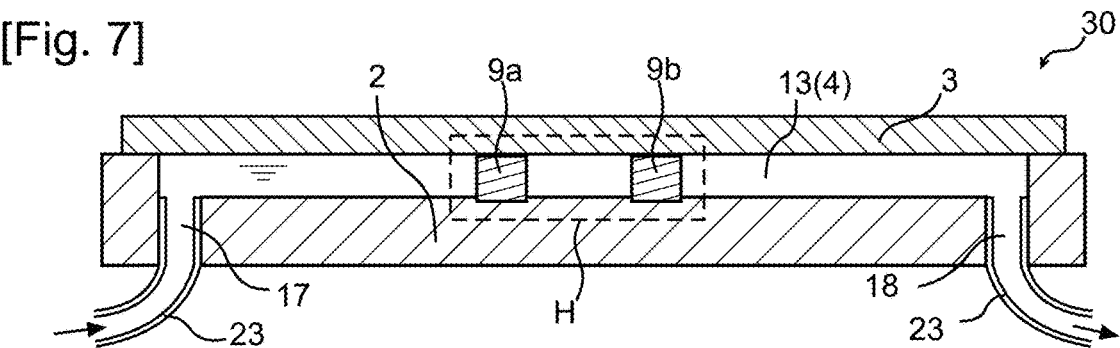
[Fig. 8]
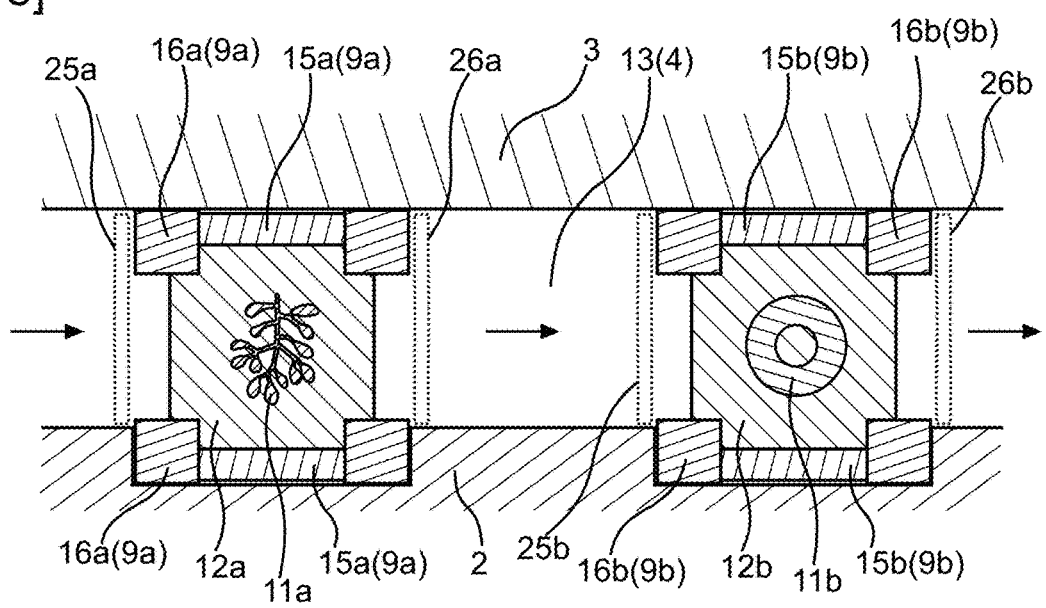

[Fig. 9]
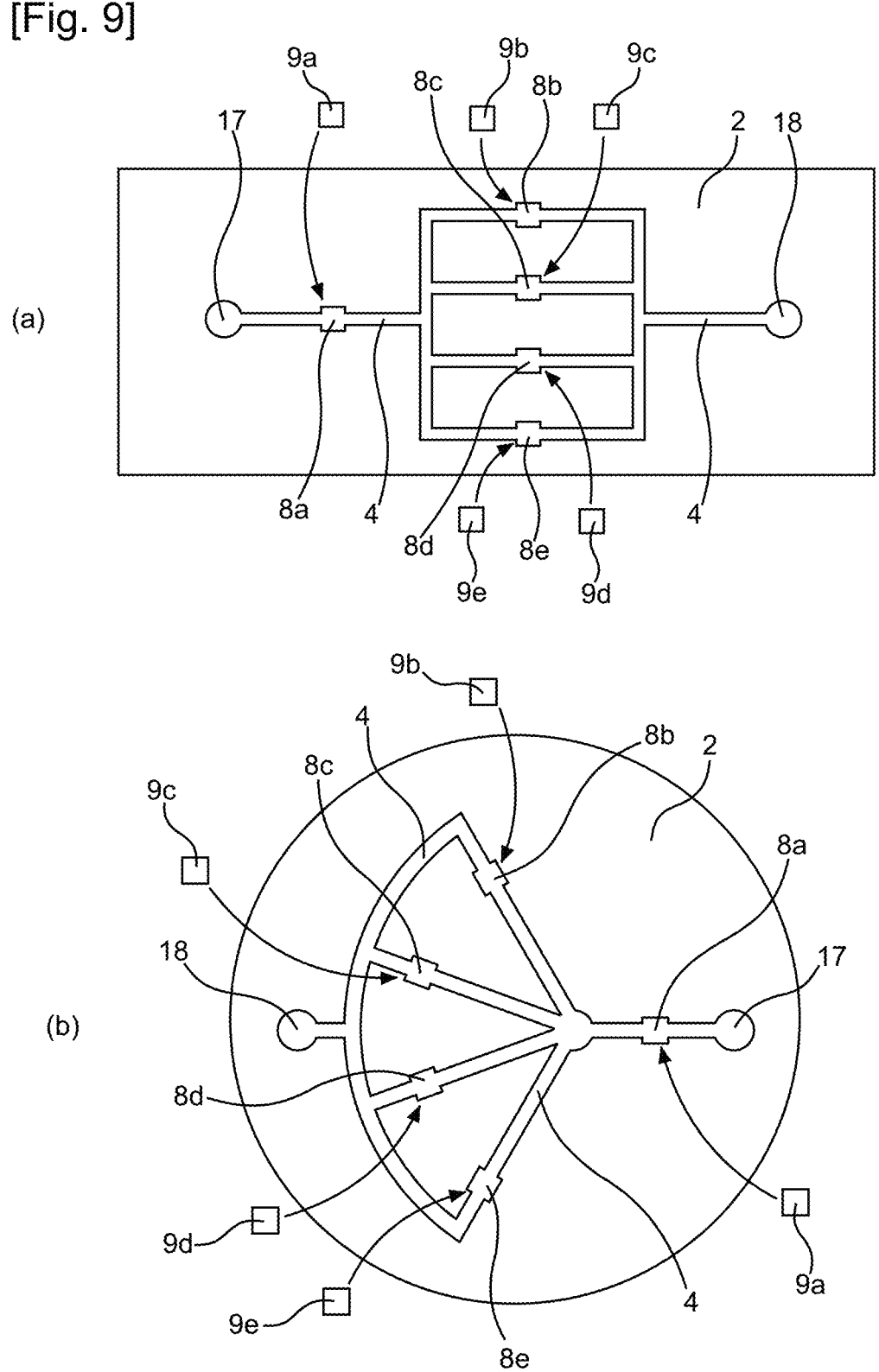

[Fig. 10]
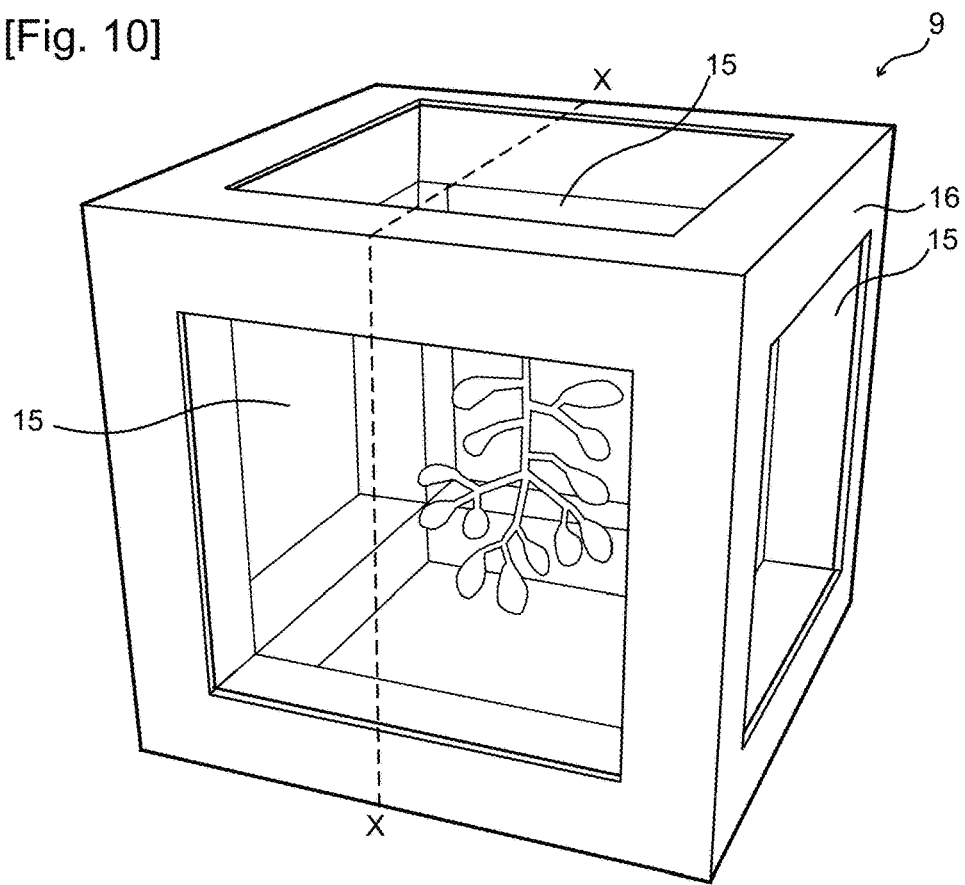
[Fig. 11]
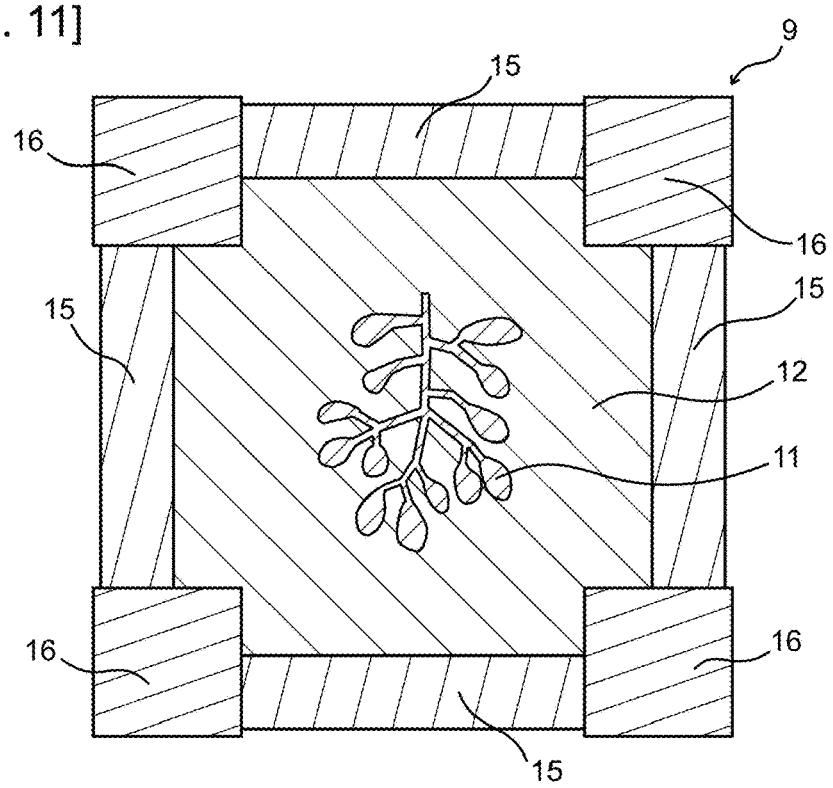

[Fig. 12]
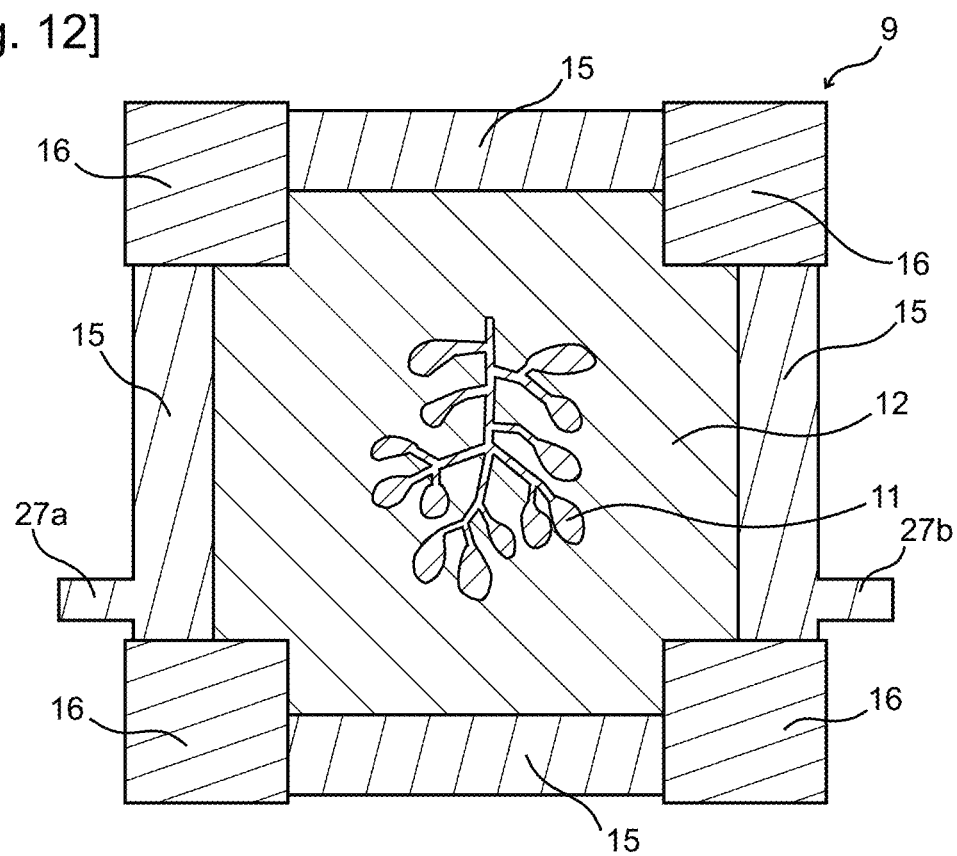

[Fig. 13]
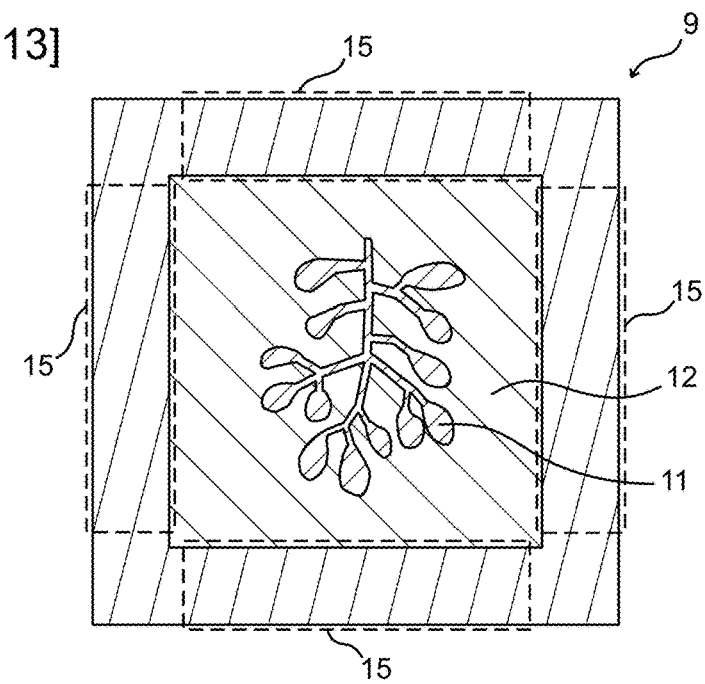
[Fig. 14]
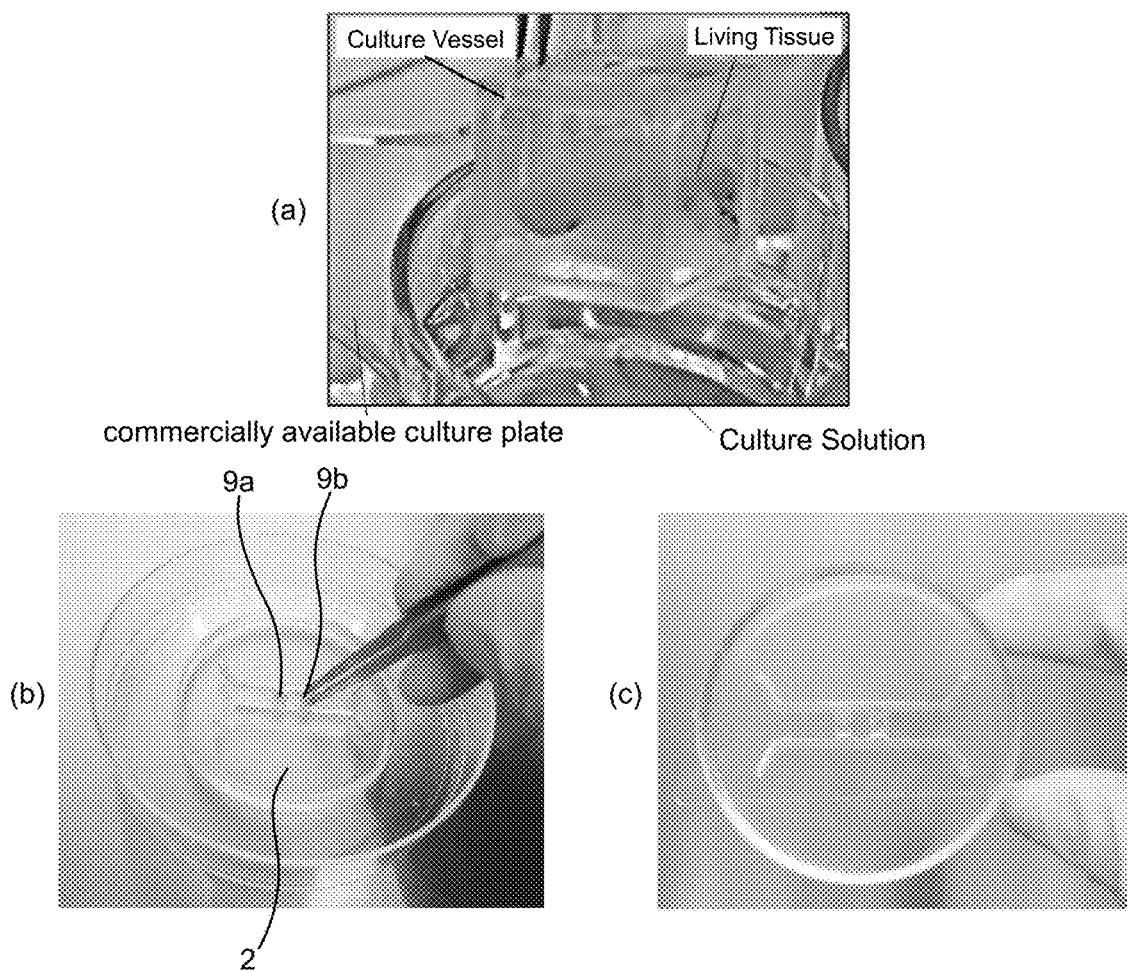

[Fig. 15]
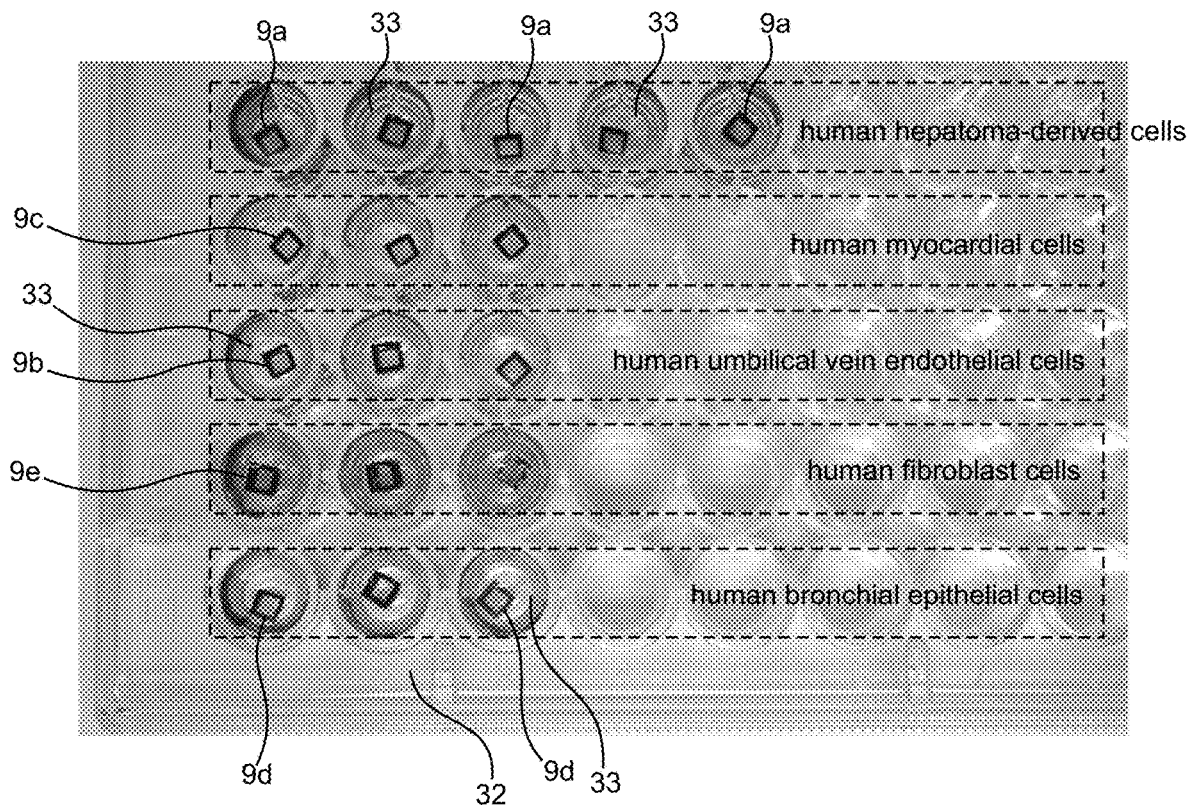
[Fig. 16]
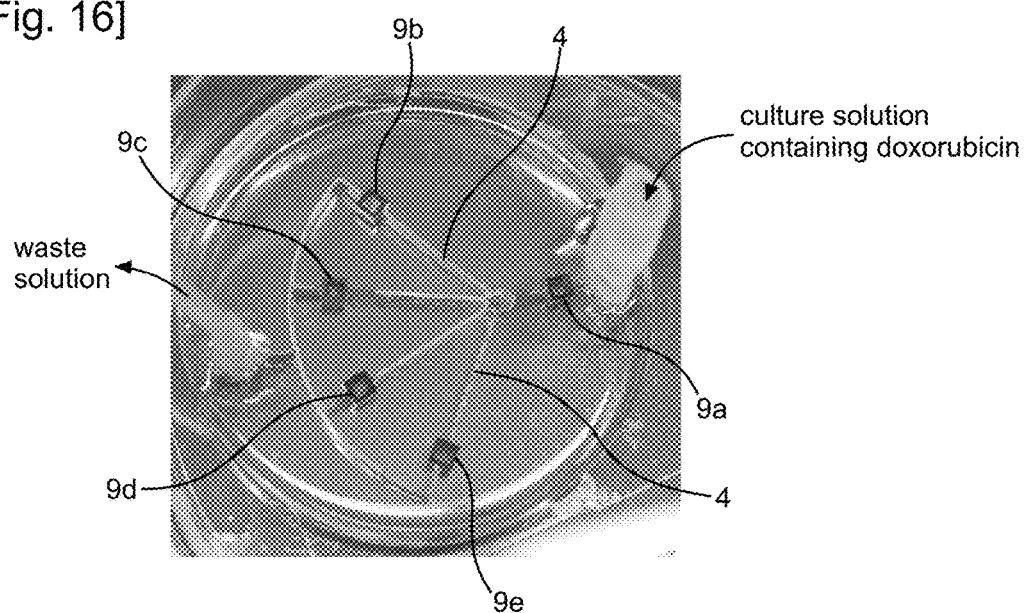

[Fig. 17]
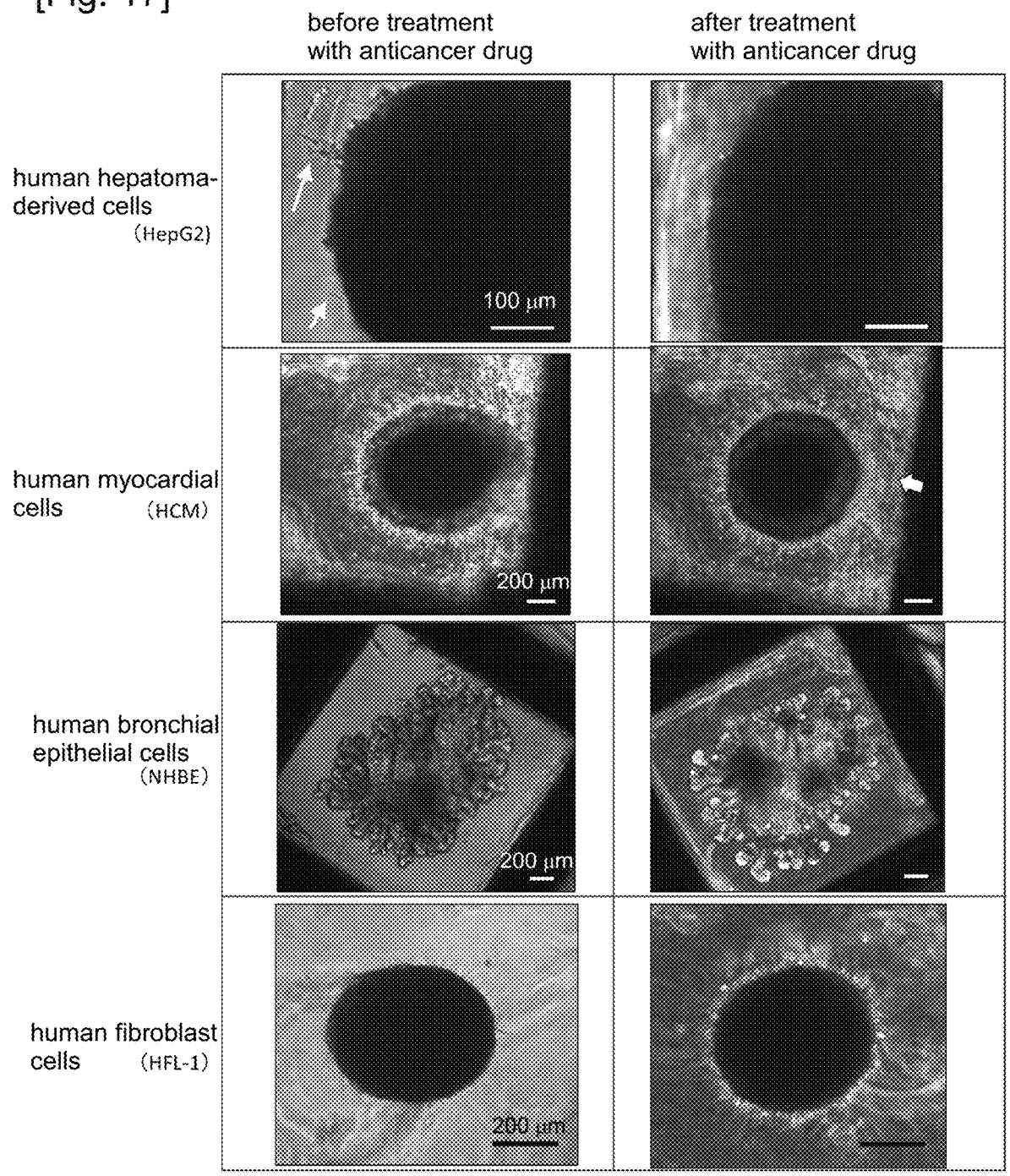

FLUIDIC CHIP FOR CELL CULTURE USE, CULTURE VESSEL, AND CULTURE METHOD

TECHNICAL FIELD

The present invention relates to a fluidic chip for cell culture use, a culture vessel, and a culture method.

BACKGROUND ART

Studies have been conducted on formation of three-dimensionally cultured skin tissue by culturing cell tissue in three dimensions in a culture gel (see, for example, Patent Literature 1). In these studies, cell suspension sol prepared by adding dermal fibroblast to culture sol is placed into a culture dish and allowed to stand for two hours in a carbon dioxide incubator so as to gelatinize the cell suspension sol. Perfusion culture of the cell tissue is performed by supplying a culture solution to the culture dish using a silicon tube connected to the culture dish and by discharging the culture solution using another silicon tube. Due to the perfusion culture of the cell tissue in this manner, oxygen, nutrients, etc. can be continuously supplied to the cell tissue in the culture gel, whereby the cell tissue can be cultured in a culture environment similar to the in vivo environment.

Studies to culture cells using a fluidic chip have also been conducted (see, for example, Patent Literature 2). Due to the cell culture using a fluidic chip, flow path design is enabled, and precise and quantitative control for a cell culture environment is enabled.

Studies have also been conducted to mimic a microenvironment of cells or a dynamic environment such as a blood flow in a living body by utilizing a microfluidic device (see, for example, Patent Literature 3). Such a microfluidic chip is called an organ-on-a-chip or a body-on-a-chip, and is expected to be used in a preclinical test in, for example, drug development as a device for directly assessing interactions between tissues or organs.

CITATION LIST

Patent Literatures

PTL 1: Japanese Unexamined Patent Application Publication No. 2014-113118
PTL 2: Japanese Unexamined Patent Application Publication No. 2008-519598
PTL 3: Japanese Translation of PCT International Application Publication No. 2016-533184

SUMMARY OF INVENTION

Technical Problems

In perfusion culture using a culture dish, the flow path design is difficult, and fluid control is difficult, which makes it impossible to precisely and quantitatively control a cell culture environment.

In the conventional cell culture using a fluidic chip, it is necessary that, preparatory for culture, cells and culture sol are injected and crosslinked (gelatinized) in the fluidic chip, which takes time before the cell culture is started. Therefore, in the preparation stage for the cell culture, the activity of the cultured cells may be decreased, which may vary the experimental results. Further, it is difficult to collect and store the cell tissue cultured in the fluidic chip without being damaged. Moreover, the cell tissue is limited to be observed from the upper side or the lower side of the fluidic chip, which makes it difficult to find out the three-dimensional structure of the cultured cell tissue.

The conventional organ-on-a-chip needs to culture a plurality of kinds of cells in a flow path of a microchip to reproduce the dynamic environment in vivo, and thus, it requires much labor and time to reproduce the in vivo environment. Further, it is difficult to reproduce a complex in vivo environment with all cell tissues being not deteriorated. In a case where a plurality of kinds of cells is cultured in the microchip, it is also difficult to change the culture environment for each kind of cells, and therefore, it is difficult to efficiently culture cells.

In view of such circumstances, the present invention provides a fluidic chip for cell culture use which can prevent a decrease in the activity of cultured cells in a preparation stage, and which makes it possible to observe a cultured cell tissue while detaching the cultured cell tissue from the fluidic chip.

Solutions to Problems

The present invention provides a fluidic chip for cell culture use characterized by being provided with a base and a lid member, wherein the base and the lid member are configured in such a manner that a first flow path and a first accommodation section for detachably accommodating a first culture vessel are formed between the base and the lid member when the base and the lid member are bonded to each other, the first culture vessel encloses a culture gel into which cells or a cell tissue is to be embedded and is at least partially formed from a hydrogel or a porous body, and the base and the lid member are arranged in such a manner that at least a portion of a culture solution flowing through the first flow path is supplied to the first accommodation section.

Advantageous Effects of Invention

The base and the lid member included in the fluidic chip according to the present invention are configured in such a manner that a first flow path and a first accommodation section for detachably accommodating a first culture vessel therein are formed between the base and the lid member when the base and the lid member are bonded to each other. Thus, the first flow path and the first accommodation section can be formed inside the fluidic chip.

The base and the lid member are configured in such a manner that at least a portion of a culture solution flowing through the first flow path is supplied to the first accommodation section. The first culture vessel housed in the first accommodation section encloses a culture gel into which cells or a cell tissue is embedded and is at least partially formed from a hydrogel or a porous body. With this configuration, when the culture solution is introduced into the first flow path, the culture solution can be supplied to the first accommodation section. Thus, nutrients, proteins, chemical substances, oxygen, etc. contained in the culture solution can be supplied to the cell tissue via the first culture vessel (hydrogel or porous body) and the culture gel, and the cell tissue in the culture vessel can be cultured. In addition, stimulus factors, growth factors, etc. contained in the culture solution can also be supplied to the cell tissue, whereby the effect of the stimulus factors, growth factors, etc. on the cell tissue can be examined. Further, the in vivo environment (blood flow, etc.) can be reproduced by the culture solution flowing through the first flow path.

The first accommodation section is provided for detachably accommodating the first culture vessel, whereby the first culture vessel can be attached to and detached from the first accommodation section. Accordingly, the first culture vessel which is prepared in advance can be attached to the first accommodation section at an optional timing, which can prevent the cell tissue from being deteriorated before the start of culture in the fluidic chip. Further, the time required for experiments can be shortened, and thus, an occurrence of variation in experimental results can be prevented. Since the first culture vessel can be attached to the first accommodation section after cells or cell tissue in the first culture vessel are preparatorily cultured in an optimum culture environment, the cell tissue that is not deteriorated can be placed in the fluidic chip. Thus, in a case where a plurality of kinds of cell tissues are placed in the fluidic chip, each of the cell tissues can also be placed in the fluidic chip without being deteriorated, whereby a complex in vivo environment including a variety of cell tissues can also be easily reproduced. In addition, after cells or cell tissues are preparatorily cultured in a plurality of first culture vessels, respectively, and then, the satisfactory first culture vessel can be selected from among the plurality of first culture vessels used for the preparatory culture, and the selected first culture vessel can be placed in the fluidic chip. This makes it possible to place the cells or cell tissue suitable for experiments into the fluidic chip, whereby the in vivo environment can be reproduced with excellent reproducibility.

After the cell culture in the fluidic chip is completed, and the lid member is removed from the base, the first culture vessel housed in the first accommodation section can be detached from the first accommodation section, and the cultured cell tissue can be observed with a microscope or the like with the first culture vessel being detached from the fluidic chip. Therefore, the cell tissue can be observed from various directions, whereby the three-dimensional structure of the cultured cell tissue can be easily recognized. In addition, the cell tissue cultured in the fluidic chip can be easily collected and stored without being damaged.

BRIEF DESCRIPTION OF DRAWINGS

FIG. 1 is a top view schematically illustrating a fluidic chip according to one embodiment of the present invention.

FIG. 2(a) is a schematic sectional view of the fluidic chip taken along a broken line A-A in FIG. 1, FIG. 2(b) is a schematic sectional view of the fluidic chip taken along a broken line B-B in FIG. 1, FIG. 2(c) is a schematic sectional view of the fluidic chip taken along a dot-and-dash ling C-C in FIG. 1, and FIG. 2(d) is a schematic sectional view of the fluidic chip taken along a dot-and-dash ling D-D in FIG. 1.

FIG. 3 is a top view schematically illustrating a fluidic chip according to one embodiment of the present invention.

FIG. 4(a) is a schematic sectional view of the fluidic chip taken along a broken line E-E in FIG. 3, FIG. 4(b) is a schematic sectional view of the fluidic chip taken along a broken line F-F in FIG. 3, FIG. 4(c) is a schematic sectional view of the fluidic chip taken along a dot-and-dash ling G-G in FIG. 3, and FIG. 4(d) is a schematic sectional view of the fluidic chip taken along a dot-and-dash ling H-H in FIG. 3.

FIGS. 5(a) and 5(b) are top views schematically illustrating a fluidic chip according to one embodiment of the present invention.

FIG. 6 is a top view schematically illustrating a fluidic chip according to one embodiment of the present invention.

FIG. 7 is a sectional view schematically illustrating a fluidic chip according to one embodiment of the present invention.

FIG. 8 is a schematic enlarged view of a portion H of the fluidic chip enclosed by a broken line in FIG. 7.

FIGS. 9(a) and 9(b) are top views schematically illustrating a fluidic chip according to one embodiment of the present invention.

FIG. 10 is a perspective view schematically illustrating a culture vessel to be housed in an accommodation section of a fluidic chip according to one embodiment of the present invention.

FIG. 11 is a schematic sectional view of the culture vessel taken along a broken line X-X in FIG. 10.

FIG. 12 is a sectional view schematically illustrating a culture vessel according to one embodiment of the present invention.

FIG. 13 is a sectional view schematically illustrating a culture vessel to be housed in an accommodation section of a fluidic chip according to one embodiment of the present invention.

FIG. 14(a) is a photograph of a manufactured culture vessel, and FIGS. 14(b) and 14(c) are photographs of a fluidic chip accommodating the manufactured culture vessel.

FIG. 15 is a photograph of a multi-well plate accommodating a plurality of culture vessels, each enclosing cells preparatorily cultured in a cell culture experiment.

FIG. 16 is a photograph of a fluidic chip accommodating various kinds of culture vessels.

FIG. 17 illustrates photographs of various cells before and after they are cultured using a culture solution containing doxorubicin.

DESCRIPTION OF EMBODIMENTS

The fluidic chip according to the present invention is characterized by being provided with a base and a lid member, wherein the base and the lid member are configured in such a manner that a first flow path and a first accommodation section for attachably/detachably accommodating a first culture vessel are formed between the base and the lid member when the base and the lid member are bonded to each other, the first culture vessel encloses a culture gel into which cells or a cell tissue is to be embedded and is at least partially formed from a hydrogel or a porous body, and the base and the lid member are configured in such a manner that at least a portion of a culture solution flowing through the first flow path is supplied to the first accommodation section.

It is desirable that the base or the lid member included in the fluidic chip according to the present invention has a first inlet and a first outlet, and the first flow path is provided in such a manner that the culture solution injected through the first inlet flows through the first flow path and is discharged through the first outlet. It is possible to allow the culture solution to flow through the first flow path by injecting the culture solution into the first inlet.

It is desirable that the first accommodation section has a socket (receiving part) with which the first culture vessel is engageable. The culture vessel can be fixed to the accommodation section by inserting the culture vessel into the socket. Further, the culture vessel can be removed from the accommodation section by extracting the culture vessel from the socket.

It is desirable that the base and the lid member are configured in such a manner that a second flow path is formed between the base and the lid member when the base and the lid member are bonded to each other, and the base or the lid member has a second inlet and a second outlet. It is also desirable that the second flow path is provided in such a manner that a culture solution or a normal saline solution injected through the second inlet flows through the second flow path and is discharged through the second outlet. It is also desirable that the base and the lid member are configured in such a manner that at least a portion of the culture solution flowing through the first flow path and a portion of the culture solution or the normal saline solution flowing through the second flow path are both supplied to the first accommodation section. This configuration makes it possible to allow culture solutions or normal saline solutions having different components to flow through the first flow path and the second flow path, respectively, whereby a concentration gradient of culture solution components can be formed in the accommodation section. Therefore, the effect of the concentration gradient on the cultured cell can be examined.

It is desirable that the fluidic chip according to the present invention further includes a first culture vessel housed in the first accommodation section, and the lid member to be bonded to the base, wherein the lid member is configured so as to partially serve as a flow path wall of the first flow path or an inner wall of the accommodation section. Accordingly, the cell tissue in the culture vessel can be cultured, and the leakage of the culture solution can be prevented. Further, the culture vessel can be attached to the accommodation section before the lid member is bonded to the base, and the culture vessel can be detached from the accommodation section after the lid member is peeled from the base.

It is desirable that the culture vessel has a light-permeable window made from a hydrogel or a porous body, wherein the hydrogel includes at least one selected from an agarose gel, a polyacrylamide gel, a sodium alginate, and a collagen gel, and the porous body includes at least one selected from a porous material sheet, a mesh, an etching sheet, a nonwoven fabric, and a woven fabric. With this configuration, nutrients, proteins, oxygen, etc. contained in the culture solution can be supplied to the cell tissue through the window and the culture gel. In addition, the cell tissue inside the culture vessel can be observed through the window with a microscope or the like.

It is desirable that the base and the lid member are configured in such a manner that a second accommodation section for detachably accommodating a second culture vessel is formed between the base and the lid member when the base and the lid member are bonded to each other. It is also desirable that the second culture vessel encloses a culture gel into which cells or a cell tissue is to be embedded and is at least partially formed from a hydrogel or a porous body. It is also desirable that the base and the lid member are configured in such a manner that the culture solution flowing through the first flow path permeates into and is supplied to an inside of the first culture vessel housed in the first accommodation section, and that the culture solution which has flown inside the first culture vessel as osmotic flow permeates into and is supplied to an inside of the second culture vessel housed in the second accommodation section. With this configuration, cell secretions from the cell tissue inside the first culture vessel can be supplied to the cell tissue inside the second culture vessel together with the culture solution, whereby the interaction between the cell tissue inside the first culture vessel and the cell tissue inside the second culture vessel can be examined.

It is desirable that the first accommodation section is provided in such a manner that the first culture vessel is fitted into the first accommodation section, and the second accommodation section is provided in such a manner that the second culture vessel is fitted into the second accommodation section. This makes it possible to prevent the formation of a gap through which the culture solution flows between the accommodation section and the culture vessel, which can allow the culture solution to efficiently flow inside the culture vessel as osmotic flow.

The present invention also provides a fluidic chip for cell culture use provided with a base, wherein the base has a first flow path and an accommodation section for detachably accommodating a culture vessel, the culture vessel encloses a culture gel into which cells or a cell tissue is to be embedded and is at least partially formed from a hydrogel or a porous body, and the base is configured in such a manner that at least a portion of a culture solution flowing through the first flow path is supplied to the accommodation section.

The present invention also provides a culture vessel comprising a frame that has a polyhedral shape having openings in respective faces, and windows provided in the respective faces, wherein the frame and the windows are arranged in such a manner as to allow a culture gel to be enclosed inside the frame and the windows, the windows are made from a hydrogel or a porous body having light permeability, and at least one of the windows has a protrusion protruding outwardly of the frame.

The present invention also provides a culture method comprising: preparatorily culturing cells or a cell tissue in a first culture vessel that encloses a culture gel into which the cells or the cell tissue is embedded and that is at least partially formed from a hydrogel or a porous body; placing the first culture vessel enclosing the preparatorily cultured cells or cell tissue in a first accommodation section of a fluidic chip for cell culture use; and supplying, through a first flow path, a culture solution to the cells or the cell tissue enclosed in the first culture vessel housed in the first accommodation section.

In the following, one embodiment of the present invention will be described with reference to the drawings. Note that configurations indicated in the drawings and the following descriptions are merely illustrative, and do not limit the scope of the present invention.

FIGS. 1 to 13 are views relating to a fluidic chip for cell culture use and a culture vessel according to the present embodiment, the details of which are as described in the above brief description of the drawings. FIGS. 1 and 2 illustrate a fluidic chip 30 to which a culture vessel 9 is not attached, and to which a lid member 3 is not bonded, while FIGS. 3 and 4 illustrate that the culture vessel 9 is attached to the fluidic chip 30 illustrated in FIGS. 1 and 2, the lid member 3 is bonded to a base 2, and a culture solution 13 flows through flow paths 4a and 4b. FIG. 5(a) is a top view schematically illustrating a fluidic chip 30 to which a culture vessel 9 is not attached, and FIG. 5(b) is a top view schematically illustrating the fluidic chip 30 to which the culture vessel 9 is attached. FIG. 6 illustrates a fluidic chip 30 to which a culture vessel 9 is not attached, and to which a lid member 3 is not bonded, while FIG. 7 illustrates that the culture vessel 9 is attached to the fluidic chip 30 illustrated in FIG. 6, the lid member 3 is bonded to a base 2, and a culture solution 13 flows through a flow path 4. Note that FIG. 7 is a sectional view of the fluidic chip 30 along a broken line G-G in FIG. 6. FIGS. 9(a) and 9(b) illustrate a fluidic chip 30 to which a culture vessel 9 is not attached, and to which a lid member 3 is not bonded.

The fluidic chip 30 for cell culture use according to the present embodiment is characterized by being provided with a base 2 and a lid member 3, wherein: the base 2 and the lid member 3 are configured in such a manner that a first flow path 4 and an accommodation section 8 for detachably accommodating the culture vessel 9 are formed between the base 2 and the lid member 3 when the base 2 and the lid member 3 are bonded to each other; the culture vessel 9 encloses a culture gel 12 into which cells or a cell tissue 11 is to be embedded and is at least partially formed from a hydrogel 15 or a porous body 15; and the base 2 and the lid member 3 are configured in such a manner that at least a portion of a culture solution flowing through the first flow path 4 is supplied to the accommodation section 8.

Further, the fluidic chip 30 for cell culture use according to the present embodiment is characterized by being provided with a base 2, wherein: the base 2 has a first flow path 4 and an accommodation section 8 for detachably accommodating a culture vessel 9; the culture vessel 9 encloses a culture gel 12 into which cells or a cell tissue 11 is to be embedded and is at least partially formed from a hydrogel 15 or a porous body 15; and the base 2 is configured in such a manner that at least a portion of a culture solution 13 flowing through the first flow path 4 is supplied to the accommodation section 8.

The fluidic chip 30 for cell culture use according to the present embodiment will be described below.

The fluidic chip 30 for cell culture use is a fluidic chip by which the cells or the cell tissue 11 can be cultured by allowing the culture solution 13 to flow through the flow path 4. The fluidic chip 30 for cell culture use may be a microfluidic chip, a perfusion culture device, a culture environment control device, or an organ-on-a-chip.

The fluidic chip 30 is provided with the base 2. The base 2 can be provided with the flow path 4, the accommodation section 8, and the like. The material of the base 2 may be a polymer material such as silicon rubber (for example, PDMS), acrylic resin (for example, PMMA), or polycarbonate, or may be glass. The material of the base 2 preferably has light permeability. With this configuration, the cell tissue 11 being cultured can be easily observed.

The fluidic chip 30 can be provided with the lid member 3. In a case where the flow path 4 and the accommodation section 8 are of an open type or in a case where the flow path 4 and the accommodation section 8 are formed inside the base 2, the lid member 3 can be eliminated.

The lid member 3 is, for example, a glass plate. With this configuration, the cell tissue 11 inside the culture vessel 9 can be observed from the lid member 3 side, whereby the cell tissue 11 being cultured in the fluidic chip 30 can be observed.

The lid member 3 is a member bonded to the base 2 when cells are cultured using the fluidic chip 30. The base 2 and the lid member 3 may be bonded by adhesiveness of the base 2, may be bonded by pressure welding between the base 2 and the lid member 3 using a clip or the like, may be bonded using a double-sided tape, or may be bonded by performing a plasma etching treatment on the bonded surface of the base 2 or the lid member 3. By using such methods, the base 2 and the lid member 3 can be bonded to each other without using an adhesive or a heating and melting treatment. Further, the flow path 4 formed between the base 2 and the lid member 3 can be prevented from being clogged. In addition, the formation of a gap between the base 2 and the lid member 3 can be prevented, which can prevent a leakage of the culture solution 13.

The lid member 3 can be bonded to the base 2 after the culture vessel 9 is placed into the accommodation section 8. Further, the lid member 3 can be provided in such a way as to partially serve as a flow path wall of the flow path 4 or an inner wall of the accommodation section 8.

The lid member 3 can be also provided to be peelable or removable from the base 2. With this configuration, the culture vessel 9 can be extracted from the fluidic chip 30 after the cell culture using the fluidic chip 30. It is also possible to rotate the cell tissue 11 in the fluidic chip 30.

The base 2 and the lid member 3 can be configured in such a manner that at least one flow path 4 is formed between the base 2 and the lid member 3 when the base 2 and the lid member 3 are bonded to each other. Alternatively, the base 2 may have at least one flow path 4. The flow path 4 serves as a flow path through which the culture solution 13 or a normal saline solution flows. The flow path 4 may be, for example, a groove formed in the base 2. The flow path 4 may also be a groove formed in the lid member 3. The top part of the flow path 4 having a groove shape can be closed when the base 2 and the lid member 3 are bonded to each other. The flow path 4 may also be an internal flow path of the fluidic chip 30.

The base 2 and the lid member 3 can be configured in such a manner that a plurality of flow paths 4 is formed between the base 2 and the lid member 3. This configuration makes it possible to allow culture solutions 13 having different components to flow through the flow paths 4, respectively. It is also possible to allow the culture solution 13 to flow through one flow path 4a, and allow the normal saline solution to flow through another flow path 4b. For example, the base 2 may have two flow paths 4a and 4b as in the fluidic chip 30 illustrated in FIGS. 1 to 4. Alternatively, the base 2 may have three flow paths 4a, 4b, and 4c as in the fluidic chip 30 illustrated in FIG. 5. Alternatively, the flow path 4 can be formed such that the culture solution 13 flows through the culture vessel 9 as osmotic flow as in the fluidic chip 30 illustrated in FIGS. 6 to 8. The flow path 4 may be branched into a plurality of branch paths as in the fluidic chip 30 illustrated in FIGS. 9(a) and 9(b).

The flow path 4 may be formed by machining the base 2 or the lid member 3, may be formed by casting the base 2 or the lid member 3, or may be formed by wet etching the base 2 or the lid member 3.

The flow path 4 can be formed to have an inlet 17 at one end and an outlet 18 at the other end. This enables the culture solution 13 injected through the inlet 17 to flow through the flow path 4 and to be discharged through the outlet 18. A tube 23a can be connected to the inlet 17, and a tube 23b can be connected to the outlet 18. Further, the culture solution 13 fed from a syringe pump can be injected to the inlet 17 through the tube 23a. In addition, the culture solution 13 temperature controlled by a temperature control device can be injected to the inlet 17. The inlet 17 and/or the outlet 18 may be formed in the base 2 or in the lid member 3. In addition, a drug (for example, antibiotic) can be injected through the inlet 17 together with the culture solution. Thus, the drug can be supplied to the cell tissue 11 in the culture vessel 9, whereby an effect of the drug on the cell tissue 11 can be examined. Further, when the drug is supplied to the cell tissue 11, the effect of cell secretions secreted from the cell tissue 11 on another cell tissue 11 can be examined.

In the fluidic chip 30 illustrated in FIGS. 1 to 4, a culture solution 13a introduced through an inlet 17a flows through the flow path 4a and is discharged through an outlet 18a, and a culture solution 13b introduced through an inlet 17b flows through the flow path 4b and is discharged through an outlet 18b, for example.

When the fluidic chip 30 has a plurality of flow paths 4, the plurality of flow paths 4 may share the outlet 18. For example, the base may be configured in such a manner that the culture solution flowing through the first flow path 4 and the culture solution 13 flowing through the second flow path 4 converge, and the confluent culture solution 13 is discharged through the single outlet 18.

As in the fluidic chip 30 illustrated in FIG. 6, the fluidic chip 30 may be provided with a circulation flow path 5 for circulating the culture solution by returning a portion of the culture solution from the downstream side to the upstream side of the flow path 4. When the culture solution is circulated through the flow path 4 and the circulation flow path 5 by, for example, providing a backflow prevention valve 6 in the circulation flow path 5, blood circulation in a living body can be reproduced.

The base 2 and the lid member 3 can be arranged in such a manner that at least one accommodation section 8 for detachably accommodating the culture vessel 9 therein is formed between the base 2 and the lid member 3 when the base 2 and the lid member 3 are bonded to each other. If the accommodation section 8 is provided between the base 2 and the lid member 3 so as to close the upper part of the accommodation section 8 by the lid member 3, the culture solution 13 can be supplied while pressure is externally applied to the flow path 4 and the accommodation section 8. Further, it is possible to control the flow rate of the culture solution flowing through the flow path 4 by adjusting the pressure of the culture solution injected to the inlet 17. In addition, a wall formed from a deformable material may be provided between the flow path 4 and the accommodation section 8, for example, and due to deformation of the wall between the flow path 4 and the accommodation section 8 caused by varying the pressure of flow of the culture solution 13 flowing through the flow path 4, a dynamic stimulus can be applied to the culture vessel 9 housed in the accommodation section 8.

The base 2 may have at least one accommodation section 8. For example, the accommodation section 8 may be provided by forming a groove for forming the accommodation section 8 in the base 2 and closing the upper part of the groove by the lid member 3. Alternatively, the accommodation section 8 which is open at the top may be provided by forming a groove for forming the accommodation section 8 in the base 2.

The accommodation section 8 is a space (or a chamber) for detachably accommodating the culture vessel 9 therein. The accommodation section 8 may be a groove formed in the base 2 or a groove formed in the lid member 3. With this configuration, the culture vessel 9 can be placed into the accommodation section 8 from above the groove, or the culture vessel 9 placed in the accommodation section 8 can be removed. The upper part of the accommodation section 8 having the groove shape can be closed by bonding the base member 2 and the lid member 3 to each other.

Regarding the position of the accommodation section 8 between the base 2 and the lid member 3, the accommodation section 8 can be provided in the flow path 4 so that most of the culture solution flowing through the flow path 4 passes through the accommodation section 8. Although both ends of the accommodation section 8 are connected to the flow paths 4a and 4b, respectively, in the example illustrated in FIGS. 1 to 4, the accommodation section 8 can be provided in the flow path 4 so that most of the culture solution flowing through the flow path 4 passes through the accommodation section 8.

Alternatively, the accommodation section 8 may be provided at a position distant from the flow path 4, and a communication flow path connecting the accommodation section 8 and the flow path 4 may be provided. In this case, most of the culture solution flowing through the flow path 4 do not pass through the accommodation section 8, and a portion of the culture solution is supplied to the accommodation section 8 through the communication flow path.

The accommodation section 8 may be formed by machining the base 2 or the lid member 3, may be formed by casting the base 2 or the lid member 3, or may be formed by wet etching the base 2 of the lid member 3.

The fluidic chip 30 may be provided with a plurality of accommodation sections 8. Further, the base 2 and the lid member 3 may be configured in such a manner that a plurality of culture vessels 9 can be housed in a single accommodation section 8. This makes it possible to attach the plurality of culture vessels 9 to the fluidic chip 30, whereby interaction between cells of the cell tissues 11 in the culture vessels 9 can be examined. The cell tissues 11 in the plurality of culture vessels 9 may be of the same type or different types.

The base 2 and the lid member 3 are configured in such a manner that at least a portion of the culture solution 13 or the normal saline solution flowing through the flow path 4 is supplied to the accommodation section 8. For example, the accommodation section 8 may be provided in the flow path 4, and the flow path 4 and the accommodation section 8 may be arranged to allow a portion of the culture solution 13 or the normal saline solution flowing through the flow path 4 to flow into the accommodation section 8. In addition, the flow path 4 and the accommodation section 8 may be connected by means of a communication flow path.

The plurality of flow paths 4 and the accommodation section 8 may be arranged to allow a portion of the culture solution 13 or the normal saline solution flowing through the plurality of flow paths 4 to flow into the accommodation section 8. When the accommodation section 8 is provided as described above, it is possible to allow the culture solutions 13 having different components such as stimulus factors to flow through the plurality of flow paths 4 and to allow the components of the respective culture solutions 13 to flow into the accommodation section 8. Thus, a concentration gradient of the components of the culture solutions can be formed in the accommodation section 8. Due to the formation of the concentration gradient of the components of the culture solutions in this manner, the effect of the components of the culture solutions on the cell tissue 11 can be examined.

The accommodation section 8 may be provided in the communication flow path connecting the flow path 4a and the flow path 4b. For example, when the culture solution 13a containing a component A flows through the flow path 4a, and the culture solution 13b not containing the component A flows through the flow path 4b in the fluidic chip 30 illustrated in FIGS. 3 and 4, a concentration gradient of the component A can be formed in the accommodation section 8. The effect of the component A of the culture solution on the cell tissue 11 can be examined by observing the cell tissue 11 cultured in such a culture environment. The component A can be a stimulation factor such as cytokine or hormone. This makes it possible to examine the effect of the cell stimulation on the cultured cell.

The accommodation section 8 may be provided to be connected to a flow path 4a, a flow path 4b, and a flow path 4c. For example, when a culture solution 13a containing a component A flows through the flow path 4a, a culture solution 13b containing a component B flows through the flow path 4b, and a culture solution 13c containing a component C flows through the flow path 4c in the fluidic chip 30 illustrated in FIG. 5, concentration gradients of the components A, B, and C can be formed in the accommodation section 8. The effect of the components A, B, and C of the culture solutions on the cell tissue 11 can be examined by observing the cell tissue 11 cultured in such a culture environment.

The accommodation section 8 can be provided with a socket 20 to which the culture vessel 9 can be fitted and fixed.

When the culture vessel 9 is fitted into the socket 20, the culture vessel 9 can be fixed to the accommodation section 8, so that the displacement of the culture vessel 9 can be prevented. Further, the culture vessel 9 can be detached from the accommodation section 8 by removing the culture vessel 9 from the socket 20.

The socket 20 may be a recess formed in the inner surface of the accommodation section 8. For example, the socket 20 may have a shape into which the bottom part of the culture vessel 9 is just fitted as in the fluidic chip 30 illustrated in FIGS. 1 to 4, or may have a groove shape as long as it can hold and fix the bottom part of the culture vessel 9.

Alternatively, the socket 20 may be formed by a plurality of protrusions 22. For example, in the fluidic chip 30 illustrated in FIG. 5, a space is formed around the culture vessel 9 housed in the accommodation section 8 so as to allow circulation of the culture solution, and a plurality of protrusions 22a to 22h is provided to the accommodation section 8. The culture vessel 9 is held by the plurality of protrusions 22a to 22h in the vicinity of four sides of the culture vessel 9. Thus, the culture vessel 9 can be affixed at a fixed position in the accommodation section 8.

Note that the socket (recess, protrusion) for receiving and fixing the culture vessel 9 may be provided in the lid member 3, instead of being provided in the base 2.

The base 2 and the lid member 3 can be configured in such a manner that the culture solution 13 flowing through the flow path 4 permeates into and is supplied to the inside of a culture vessel 9a (culture gel 12a and cell tissue 11a) housed in a accommodation section 8a, and the culture solution 13 that has flown inside the culture vessel 9a as osmotic flow permeates into and is supplied to the inside of a culture vessel 9b (culture gel 12b and cell tissue 11b) housed in a accommodation section 8b. This makes it possible to supply cell secretions from the cell tissue 11a inside the culture vessel 9a to the cell tissue 11b inside the culture vessel 9b together with the culture solution 13, whereby the interaction between the cell tissue 11a and the cell tissue 11b can be examined. For example, a bronchial tissue can be used as the cell tissue 11a, and a heart tissue can be used as the cell tissue 11b. In such a case, the effect of cell secretions from the bronchial tissue on the heart tissue can be examined.

For example, as in the fluidic chip 30 illustrated in FIGS. 6 to 8, the accommodation section 8 and the culture vessel 9 can be configured to match in shape so that the culture vessel 9 is fitted into the accommodation section 8. The accommodation section 8 can be configured in such a manner that the culture solution flows therein through an inflow port 25 formed on the side surface of the accommodation section 8 and the culture solution flows out of the accommodation section 8 through an outflow port 26 formed on another side surface of the accommodation section 8. The arrangement of the accommodation section 8 as described above can allow the culture solution at the inflow port 25 to permeate into a window 15 of the culture vessel 9 or the culture gel 12. Further, this arrangement also allows the culture solution included in the culture gel 12 and leaching from another window 15 or from the culture gel to flow out through the outflow port 26. In this manner, it is possible to allow the culture solution to flow through the culture gel 12 inside the culture vessel 9 as osmotic flow.

The inner wall of the accommodation section 8 and the culture vessel 9 can be in contact with each other in order to prevent the formation of a culture solution flow path between the culture vessel 9 and the base 2 or the lid member 3. This makes it possible to allow the culture solution to efficiently flow through the culture gel 12 inside the culture vessel 9 as osmotic flow.

In a case where the culture vessel 9 has a polyhedral frame 16 having openings on the respective faces, a window 15 provided in at least one of the plurality of openings, and the culture gel 12 placed inside the frame 16 and the window 15, the culture solution may be in direct contact with the culture gel without providing the window 15 in the first opening of the frame 16 adjacent to the inflow port 25 of the culture solution and the second opening of the frame 16 adjacent to the outflow port 26. This makes it possible to allow the culture solution to efficiently flow through the culture gel 12 inside the culture vessel 9 as osmotic flow.

For example, the culture vessel 9a can be housed in the accommodation section 8a, and the culture vessel 9b can be housed in the accommodation section 8b as illustrated in FIG. 8. This makes it possible to allow the culture solution injected through the inlet 17 to flow, as osmotic flow, through the culture gel 12 inside the culture vessel 9a placed in the accommodation section 8a, and then, to flow through the culture gel 12 inside the culture vessel 9b placed in the accommodation section 8b as osmotic flow. The method for allowing the culture solution to flow inside the culture vessel 9 as osmotic flow is as described above.

Different cell tissues (for example, different types of cell tissues, or abnormal cells and normal cells) can be used as the cell tissue 11a and the cell tissue 11b. For example, the cell tissue 11a is a bronchial tissue, and the cell tissue 11b is a heart tissue. Alternatively, the cell tissue 11a includes cancer cells, and the cell tissue 11b includes normal cells, for example. In such a case, the effect of secretions of the cancer cells on the normal cells can be examined.

The base 2 and the lid member 3 may be configured in such a manner that a culture solution 13 flowing through a flow path 4 permeates into and is supplied to the inside of a culture vessel 9a housed in an accommodation section 8a, and the culture solution 13 which has flown through the inside of the culture vessel 9a as osmotic flow permeates into and is supplied to the inside of a culture vessel 9b housed in an accommodation section 8b and the inside of a culture vessel 9c housed in an accommodation section 8c. This makes it possible to simultaneously examine the effects of cell secretions from the cell tissue 11a inside the culture vessel 9a on the cell tissue 11b inside the culture vessel 9b and on the cell tissue 11c inside the culture vessel 9c. The method for allowing the culture solution to flow inside the culture vessel 9 as osmotic flow is as described above.

For example, as in the fluidic chip 30 illustrated in FIGS. 9(a) and 9(b), the flow path 4 and the accommodation section 8 can be arranged in such a manner that the culture solution injected through the inlet 17 flows inside the culture vessel 9a placed in an accommodation section 8a as osmotic flow, and then, flows, as osmotic flow, inside a culture vessel 9b placed in an accommodation section 8b, inside a culture vessel 9c placed in an accommodation section 8c, inside a culture vessel 9d placed in an accommodation section 8d, and inside a culture vessel 9e placed in an accommodation section 8e.

The culture vessel 9 encloses the culture gel 12 into which a cell or the cell tissue 11 is to be embedded. The culture vessel 9 is at least partially formed from a hydrogel 15 or a porous body 15. When the culture vessel 9 thus configured is housed in the accommodation section 8, the culture vessel 9 can be immersed into the culture solution 13 supplied to the accommodation section 8 through the flow path 4. Therefore, nutrients, proteins (having a molecular weight of tens of thousands to hundreds of thousands), oxygen, and the like contained in the culture solution 13 can be supplied to the cell tissue 11 via the culture vessel 9 (the hydrogel 15 or the porous body 15) and the culture gel 12, and the cell tissue 11 in the culture vessel 9 can be cultured.

In addition, the culture vessel 9 before being placed into the fluidic chip 30 can be immersed into the culture solution 13 in the culture dish or the well plate, and the nutrients, proteins, oxygen, and the like contained in the culture solution 13 in a culture dish or a well plate can be supplied to the cell tissue 11 via the culture vessel 9 (hydrogel 15) and the culture gel 12. Therefore, the culture vessel 9 can be immersed into the culture solution 13 just before it is placed into the fluidic chip 30, whereby a decrease in cell activity of the cell tissue 11 can be prevented.

In a case where different types of cell tissues 11 are placed into the fluidic chip 30, an A-type cell tissue is embedded in the culture gel inside the first culture vessel 9a, and the cell tissue inside the first culture vessel 9a can be cultured under a culture condition suitable for the A-type cell tissue, while a B-type cell tissue is embedded in the culture gel inside the second culture vessel 9b, and the cell tissue inside the second culture vessel 9b can be cultured under a culture condition suitable for the B-type cell tissue. Then, the first culture vessel 9a and the second culture vessel 9b can be placed into the accommodation section 8a and the accommodation section 8b, respectively, just before an experiment using the fluidic chip is started. Therefore, the experiment can be conducted using the A-type cell tissue which is not deteriorated and the B-type cell tissue which is not deteriorated. In the above description, the A-type cell tissue and the B-type cell tissue are used. However, it is possible to place more types of cell tissues into the fluidic chip and to conduct an experiment in a similar manner.

The culture gel 12 inside the culture vessel 9 is to culture the cells or the cell tissue 11 embedded therein. The cells 11 to be embedded in the culture gel 12 may be a cell tissue having a structure where the cells aggregate in a specific pattern, or may be cells that do not have such a tissue structure. The cells 11 without having the tissue structure may be cultured to grow into cell tissue 11. The culture gel 12 can function as a scaffold for the cell tissue 11, and can allow the cell tissue 11 to grow in three dimensions.

The culture gel 12 can contain, for example, any of collagen, laminin, entactin, and proteoglycan. The culture gel 12 can also contain, for example, any of a TGF-β, a fibroblast growth factor, and a tissue plasminogen activator. For example, Matrigel™ can be used as the culture gel 12.

The culture gel 12 is enclosed in the culture vessel 9 and is not directly in contact with the culture solution 13 supplied through the flow path 4, which can prevent deviation of the cell tissue 11 from its relative position caused by the culture gel 12 absorbing the culture solution 13 and swelling. Further, the deformation of the culture gel 12 by the flow of the culture solution 13 can be prevented, whereby deviation of the cell tissue 11 from its relative position can be prevented. In addition, in a preparation stage (preparatory culture) of the cell tissue 11, the window 15 is provided so as to prevent the culture gel 12 from being in direct contact with the culture solution 13, and at least one of the plurality of windows 15 can be removed before the culture vessel 9 is placed into the accommodation section 8. This makes it possible to prevent the culture gel 12 from swelling during the preparatory culture of the cell tissue 11. Therefore, in the experiment using the fluidic chip 30, the culture solution can be brought into contact with and permeated into the culture gel 12 inside the culture vessel 9 from the portion where the window 15 is removed, and the culture solution can be supplied to the culture gel 12 as osmotic flow. Note that, if the time required for the culture is relatively short, the culture gel 12 does not swell so much.

The culture vessel 9 is provided to enclose the culture gel 12. The space in the culture vessel 9 is filled with the culture gel 12 in which the cell tissue 11 is embedded. This makes it possible to confine the culture gel 12 and the cell tissue 11 in the culture vessel 9, and can prevent the culture gel 12 from moving inside (or drifting in) the culture vessel 9 and can also prevent the cell tissue 11 from deviating from its relative position. Since the cell tissue 11 and the culture gel 12 are placed inside the culture vessel 9 as described above, the culture gel 12, in which the cell tissue 11 is embedded, can be easily handled.

The culture gel 12 and the cell tissue 11 can be easily placed into the fluidic chip 30 by attaching the culture vessel 9 to the accommodation section 8. Further, the culture gel 12 and the cell tissue 11 can be easily taken out from the fluidic chip 30 by removing the culture vessel 9 from the accommodation section 8.

The culture vessel 9 may be, for example, polyhedral in shape. This allows the culture vessel 9 to be stably housed in the accommodation section 8. The culture vessel 9 may have a cubic shape as illustrated in FIGS. 10 and 11, or may have a cubic shape, a hexagonal column shape, or a circular cylindrical shape. The culture vessel 9 can be sized in such a way that each side of the vessel is, for example, 1 mm or longer to 5 cm or shorter in length. The culture vessel 9 may be, for example, 1 µL or higher to 10 mL or lower in volume.

The culture vessel 9 can be configured to have a light-permeable window 15 made from the hydrogel or the porous body. The window 15 has light permeability and nutrient permeability, and can be provided such that the cells or the cell tissue 11 embedded in the culture gel 12 can be observed from each of the plurality of faces. Nutrients, proteins, oxygen, and the like contained in the culture solution 13 can be supplied to the cell tissue 11 via the window 15 and the culture gel 12. Further, after the fluidic chip 30 is removed from the culture vessel 9, the cell tissue 11 inside the culture vessel 9 can be observed through the window 15 with, for example, a microscope. In a case where the culture vessel 9 is polyhedral in shape, the window 15 can be provided to each face of the culture vessel 9. This makes it possible to observe the cell tissue 11 inside the culture vessel 9 from each face of the culture vessel 9. Therefore, a three-dimensional structure of the cell tissue 11 can be identified. For example, the window 15 can be provided to each face of the culture vessel 9 as illustrated in FIGS. 10 and 11. To observe the cell tissue 11 through the windows 15, the culture vessel 9 may be placed in a glass vessel that is high in light permeability. This can prevent the culture solution, etc. to adhere to the microscope.

The culture vessel 9 can be rotated in such a way as to prevent the cell tissue 11 from deviating from its relative position, and thus can be rotated in such a way that each face of the culture vessel 9 where the window 15 is placed can function as the observation surface. Particularly, it is possible to turn over an upper surface and a lower surface of the culture vessel 9 and to turn over the culture vessel 9 sideways. Such rotations allow the cell tissue 11 inside the culture vessel 9 to be observed from each face, and make it easy to find out a three-dimensional stereoscopic geometry of the cell tissue 11. The microscope used for observing the cell tissue 11 may be an optical microscope or a laser microscope.

In the case where the culture vessel 9 has a circular cylindrical shape, the window 15 can be provided at a side surface of the circular cylinder. This makes it possible to obtain three-dimensional images of the cell tissue 11 by using the laser microscope. The window 15 may also be provided at an upper surface and a lower surface of the circular cylinder. This makes it possible to observe the cell tissue 11 from both the upper surface and the lower surface, and can improve resolution of the three-dimensional images.

The hydrogel that forms the window 15 is not particularly limited, as long as the hydrogel allows proteins to pass therethrough and has enough hardness to keep itself sustained. The hydrogel is formed by linking dispersoid in water and forming a network, and becomes a solid form in its whole system. For example, the window 15 can be configured to have the gel strength of 50 $g/cm^2$ or higher and 10000 $g/cm^2$ or lower. This can prevent the window 15 from being deformed by a weight of the culture gel 12 inside the culture vessel 9. This can also allow the window 15 to have protein permeability. The strength of the gel can be adjusted by adjusting a concentration of the dispersoid forming the network. When the concentration of the dispersoid is too low, the strength of the gel is decreased. When the concentration of the dispersoid is too high, the protein permeability is lowered. An adequate concentration of the dispersoid varies depending on the kind of the dispersoid.

For example, the hydrogel that forms the window 15 may contain, for example, an agarose gel, a polyacrylamide gel, a sodium alginate, or a collagen gel. This configuration allows the window 15 to have light permeability. This configuration also makes it possible to allow the nutrients such as proteins contained in the culture solution 13 supplied through the flow path 4 to pass through the window 15, whereby the nutrients can be supplied to the culture gel 12 and the cell tissue 11. The window 15 can be prevented from being deformed while the culture vessel 9 is rotated because the window 15 contains the agarose gel, the polyacrylamide gel, the sodium alginate, or the collagen gel. In the case where the window 15 is made from the agarose gel, the concentration of agarose may be, for example, 0.5 to 4.0%. In the case where the window 15 is made from the polyacrylamide gel, the concentration of polyacrylamide may be, for example, 3 to 20%. To form the sodium alginate-containing window 15, calcium ions are added to a sodium alginate solution so as to gelatinize the solution. To form the collagen gel-containing window 15, the collagen gel should be high in concentration. This makes it possible for the window 15 to have adequate strength.

The porous body that forms the window 15 is a member having numerous micropores. Examples of the porous body include a porous material sheet, a mesh, an etching sheet, a non-woven fabric, and a woven fabric. The porous body may have a sheet shape. Preferably, the porous body has biocompatibility. The porous body may also be made from resin such as polycarbonate, made from metal such as gold, or made from an inorganic compound such as glass. To form the window 15 formed from a porous body, a porous body sheet is bonded to the frame 16.

The culture vessel 9 may have the frame 16 bordering the window 15. This can strengthen the culture vessel 9 and makes the culture vessel 9 easy to handle. The frame can prevent damage to the window 15. As illustrated in FIGS. 10 and 11, for example, the culture vessel 9 may be constructed from the frame 16 and the windows 15. The frame 16 may be made from a biocompatible resin. The material of the frame 16 may be, for example, polycarbonate.

The culture vessel 9 as illustrated in FIGS. 10 and 11 may be manufactured as follows. A frame 16 in a cubic form having openings in six faces, respectively, are firstly set. Then, a sol for forming window is poured into the opening bordered by the frame 16 and is gelatinized to form film-shaped or sheet-shaped window 15 made from the hydrogel. In this way, a window 15 is formed at each of the five faces bordered by the frame 16. Thereafter, a yet-to-be-gelatinized culture gel and cell tissue 11 are injected into the frame 16 in the cubic form, and then, the culture gel is gelatinized. Thereafter, the sol for forming window 15 is poured into one remaining opening bordered by the frame 16 and is gelatinized to form a film-shaped or sheet-shaped window 15. As described above, the culture vessel 9 can be manufactured that encloses the cell tissue 11 and the culture gel 12.

At least one of the windows 15 included in the culture vessel 9 may have a protrusion 27 protruding outwardly of the frame 16. The window 15 can be removed from the opening of the frame 16 by pulling the protrusion 27. With this configuration, when the cell tissue 11 is preparatorily cultured, the windows 15 are provided to the openings of the frame 16, and before the culture vessel 9 is placed into the accommodation section 8, the window 15 in the opening adjacent to the inflow port 25 and the window 15 in the opening adjacent to the outflow port 26 can be removed using the protrusion 27. This makes it possible to prevent the culture gel 12 from swelling in the preparation stage of the cell tissue 11, and to allow the culture solution to flow through the culture gel 12 inside the culture vessel 9 as osmotic flow in the experiment using the fluidic chip 30. The protrusion 27 can be provided as in the culture vessel 9 illustrated in FIG. 12, for example.

The culture vessel 9 may not have any frame 16 and may be constructed from the hydrogel forming the window 15. This can prevent any blind spots that get in the way of observing the cell tissue through the window 15. Especially in the case where the culture vessel 9 is too small in size (for example, 5 mm or shorter on a side), the culture vessel 9 can be constructed without having any frame 16. Such culture vessel 9 may be manufactured as follows. Firstly, a sol for forming window 15 is poured into a mold and gelatinized to form a hollow cubic gel having one opening at one face of the cubic gel. After that, a yet-to-be-gelatinized culture gel and cell tissue 11 are injected into the cubic gel, and then, the culture gel is gelatinized. Thereafter, the sol for forming window 15 is poured into the opening of the cubic gel and is gelatinized to form a window 15. In this way, the culture vessel 9 can be manufactured that encloses the cell tissue 11 and the culture gel 12.

The fluidic chip 30 according to the present embodiment can be used as follows. First, the culture vessel 9 enclosing the culture gel 12 into which the cell tissue 11 is embedded is immersed into a culture solution to preparatorily culture the cell tissue 11. Thus, the culture vessel 9 as illustrated in FIGS. 10 and 11 is manufactured. The manufactured culture vessel 9 is attached to the accommodation section 8 of the fluidic chip 30 illustrated in FIGS. 1 and 2, and the base 2 and the lid member 3 are bonded to each other. The tube 23 is connected to the inlet 17 and the outlet 18 of the obtained fluidic chip 30, and the culture solution 13 is supplied. Thus, the fluidic chip 30 illustrated in FIGS. 3 and 4 can be manufactured. The cell tissue 11 in the culture vessel 9 can be cultured using the obtained fluidic chip 30, and the effect of the component of the culture solution on the cell tissue 11 can be examined. During the culture of the cell tissue 11, the fluidic chip 30 can be placed in an incubator.

After the culture of the cell tissue 11 using the fluidic chip 30 is completed, the lid member 3 is peeled from the base 2, and the culture vessel 9 can be extracted from the accommodation section 8. The culture vessel 9 extracted from the fluidic chip 30 is set on a microscope, and the cell tissue 11 in the culture vessel 9 can be observed. The cell tissue 11 inside the culture vessel 9 extracted from the fluidic chip 30 may be stained using a fluorescent dye, and then, fluorescently observed with a microscope. It is also possible to store the cell tissue 11 extracted from the fluidic chip 30.

The fluidic chip 30 illustrated in FIGS. 6 to 8 can be used as follows. The culture vessel 9a enclosing the culture gel 12a into which the cell tissue 11a (for example, bronchial tissue) is embedded is immersed into a culture solution to preparatorily culture the cell tissue 11a. Thus, the culture vessel 9a as illustrated in FIGS. 10 and 11 is manufactured. In parallel, the culture vessel 9b enclosing the culture gel 12b into which the cell tissue 11b (for example, heart tissue) is embedded is immersed into a culture solution to preparatorily culture the cell tissue 11b. Thus, the culture vessel 9b as illustrated in FIGS. 10 and 11 is manufactured. In the preparatory culture, the windows 15 are provided in the openings of the respective faces of the frame 16, so that the culture gel 12 and the culture solution are not in direct contact with each other.

Thereafter, the window 15 in the opening adjacent to the inflow port 25 and the window 15 in the opening adjacent to the outflow port 26 are removed using the protrusion 27, etc., and then, the culture vessel 9a is attached to the accommodation section 8a of the base 2 illustrated in FIG. 6, and the culture vessel 9b is attached to the accommodation section 8b of the base 2. Thereafter, the base 2 and the lid member 3 are bonded to each other, the tube 23 is connected to the inlet 17 and the outlet 18 of the obtained fluidic chip 30, and the culture solution 13 is supplied. Thus, the fluidic chip 30 as illustrated in FIG. 7 can be manufactured. A drug (for example, antibiotic) can be injected into the flow path 4 through the inlet 17 together with the culture solution 13. In the fluidic chip 30 described above, the culture solution 13, which permeates into the culture gel 12a inside the culture vessel 9a and flows as osmotic flow, and then, seeps out of the culture gel 12a, flows through the flow path 4, and then, permeates into the culture gel 12b inside the culture vessel 9b and flows as osmotic flow. Therefore, the effect of the drug on the cell tissues 11a and 11b and the effect of the cell secretions from the cell tissue 11a on the cell tissue 11b can be examined. When the microscope is set above the lid member 3 and the window 15, a change in the cell tissues 11a and 11b while the culture solution 13 is flowing can be observed.

The culture solution flows for a predetermined time, and then, the culture vessels 9a and 9b can be extracted from the accommodation section 8 by peeling the lid member 3 from the base 2. The culture vessels 9a and 9b extracted from the fluidic chip 30 can be set to the microscope, and the cell tissues 11a and 11b inside the culture vessels 9 can be observed.

Cell Culture Experiment (1)

A culture vessel enclosing a bronchial tissue as illustrated in FIGS. 10 and 11 was manufactured, and the manufactured culture vessel was placed into a liquid culture medium so as to culture the bronchial tissue. Firstly, a polycarbonate frame in a cubic form was prepared, 3 mm on a side, and windows were formed by using a 1.5% agarose gel. After that, Matrigel™ as a culture gel and bronchial tissue were injected into the cube, and the culture gel was gelatinized. Thereafter, a window 15 was formed in a remaining opening by using the 1.5% agarose gel. In this way, the culture vessel was manufactured. This culture vessel was placed in a liquid culture medium, and the bronchial tissue was three-dimensionally cultured for ten (10) days. Then, the bronchial tissue inside the culture vessel was observed under an optical microscope. FIG. 14(a) is a photograph of the culture vessel enclosing the cultured bronchial tissue.

Meanwhile, a fluidic chip as illustrated in FIGS. 1 and 2 was manufactured. PDMS was used as the material of the base. A glass plate was used as the lid member. The culture vessel enclosing the cultured bronchial tissue was attached to the accommodation section of the base, and the base was bonded to the lid member. FIG. 14(b) is a photograph showing that the culture vessel is attached to the accommodation section of the base, and FIG. 14(c) is a photograph of the fluidic chip after the base and the lid member are bonded to each other. Thereafter, a tube was connected to an inlet and an outlet, and a cell induction experiment was conducted by culturing the bronchial tissue inside the culture vessel for twenty-four (24) hours while a culture solution containing a growth factor was flowing through the flow path 4a and a normal saline solution was flowing through the flow path 4b. After the cell induction experiment was completed, the lid member was peeled from the base, and the culture vessel was extracted from the accommodation section. The bronchial tissue in the culture vessel was observed using an optical microscope, and was compared with the bronchial tissue not cultured using the fluidic chip, so as to examine a change of the bronchial tissue.

In this way, the effect of the culture solution component on the bronchial tissue could be examined using the fluidic chip according to the present invention.

Cell Culture Experiment (2)

Cardiac toxicity known as efficacy and side effect of doxorubicin widely used as an anticancer drug was assessed using the fluidic chip for cell culture use according to the present invention.

First, five culture vessels 9a each enclosing human hepatoma-derived cells were manufactured, three culture vessels 9b each enclosing human umbilical vein endothelial cells were manufactured, three culture vessels 9c each enclosing human myocardial cells were manufactured, three culture vessels 9d each enclosing human bronchial epithelial cells were manufactured, and three culture vessels 9e each enclosing human fibroblast cells were manufactured. These culture vessels 9a to 9e were subjected to preparatory culture (cultured in three dimensions) for two days in wells 33 of the multi-well plate 32, respectively. The culture vessels were manufactured in the same manner as in the cell culture experiment (1), except that the kinds of the cells to be cultured were changed. FIG. 15 illustrates the photograph of the multi-well plate 32 after the preparatory culture.

Thereafter, the culture vessels 9a to 9e were set on an optical microscope, and the cultured cells were observed. It was confirmed that the cells were stably grown in the culture gel 12. Then, sample cells in good condition in shape were only extracted. Then, the culture vessel 9a enclosing the human hepatoma-derived cells was inserted into the accommodation section 8a of the base 2 (made from PDMS) as illustrated in FIG. 3(b), the culture vessel 9b enclosing human umbilical vein endothelial cells was inserted into the accommodation section 8b, the culture vessel 9c enclosing human myocardial cells was inserted into the accommodation section 8c, the culture vessel 9d enclosing human bronchial epithelial cells was inserted into the accommodation section 8d, and the culture vessel 9e enclosing human fibroblast cells was inserted into the accommodation section 8e.

Thereafter, the lid member 3 (glass plate) was bonded to the base 2, and the tube 23 was connected to the inlet 17 and the outlet 18. Thus, the fluidic chip was manufactured. FIG. 16 illustrates a photograph of the manufactured fluidic chip. In the fluidic chip, the hepatoma cells were placed on the upstream of the flow path, and the myocardial cells for assessing cardiac toxicity and other normal cells as control were placed on the downstream of the flow path, so as to simulate interactions between tissues occurring in a living body.

A culture solution containing 20 μM of doxorubicin which was an anticancer drug was supplied into the manufactured fluidic chip through the inlet 17 of the fluidic chip at a constant pressure, and the culture solution was continuously supplied to the flow path of the fluidic chip for twenty-four (24) hours. Thus, the cells were cultured in three dimensions under the presence of the anticancer drug. Then, the culture vessels 9a to 9e were extracted from the fluidic chip and set on an optical microscope for observing the cultured cells. Thus, it was confirmed how the cells were changed in shape.

FIG. 17 illustrates photographs of the human hepatoma-derived cells, human myocardial cells, human bronchial epithelial cells, and human fibroblast cells before and after they were treated with the anticancer drug.

In the hepatoma cells which begin to infiltrate before the anticancer drug treatment, the infiltrating portions disappear within twenty-four hours after doxorubicin was added, and thus, the efficacy as the anticancer drug could be ascertained. It was confirmed that, regarding the bronchial epithelial cells present at the downstream side of the hepatoma cells, a branch of a bronchus was wide and continued to grow even after doxorubicin was added. It was also confirmed that, regarding the fibroblast cells present at the downstream side of the hepatoma cells, filopodia of the fibroblast extended outwardly, and the fibroblast cells continued to grow even after doxorubicin was added. Because the bronchial epithelial cells and the fibroblast cells other than the myocardial cells continued to grow as in the normal three-dimensional culture, it was confirmed that toxicity caused by enclosing these cells within the fluidic chip did not matter.

On the other hand, the myocardial cells present at the downstream side of the hepatoma cells was confirmed to be entirely reduced in size due to the anticancer drug treatment. Therefore, it was confirmed that the result which was already confirmed in two-dimensional culture and in which metabolites generated from the cancer cells under the presence of doxorubicin caused toxicity on myocardial cells also occurred in a three-dimensional culture system.

Conventionally, a high skill level is required to enclose five kinds of cells into the fluidic chip without deteriorating the cell activity, whereas the present invention makes it possible to enclose five kinds of cells into the fluidic chip within one minute. Further, when the cells were further sorted from the cells in a stable state on the second day after the start of the culture, a stable result could be obtained in a complicated experimental system with variation in cell activity which was likely to be disturbance being prevented.

REFERENCE SIGNS LIST

2 Base
3 Lid member
4, 4a, 4b, 4c Flow path
5 Circulation flow path
6 Backflow prevention valve
8, 8a, 8b, 8c, 8d, 8e Accommodation section
9, 9a, 9b, 9c, 9d, 9e Culture vessel
11, 11a, 11b Cells or cell tissue
12, 12a, 12b Culture gel
13, 13a, 13b Culture solution
15, 15a, 15b Window (hydrogel or porous body)
16, 16a, 16b Frame
17, 17a, 17b, 17c Inlet
18, 18a, 18b, 18c Outlet
20, 20a, 20b Socket (Receiving part)
22, 22a, 22b, 22c, 22d, 22e, 22f, 22g, 22h Protrusion
23, 23a, 23b, 23c, 23d Tube
25, 25a, 25b Inflow port
26, 26a, 26b Outflow port
27, 27a, 27b Protrusion
30 Fluidic chip
32 Multi-well plate
33 Well

What is claimed is:

1. A fluidic chip for cell culture use, comprising a base and a lid member, wherein
the base and the lid member are configured to define one or both of a first flow path and a first accommodation section for attachably/detachably accommodating a first culture vessel when the lid member is joined to the base,
wherein the first culture vessel comprises a culture gel having cells or a cell tissue embedded in the culture gel and includes a light-permeable window made from a hydrogel or a porous body,
wherein the light-permeable window made from the hydrogel has a gel strength of from about 50 g/cm$^2$ to about 10000 g/cm$^2$,
the first accommodation section has a socket with which the first culture vessel is engageable, and
the base and the lid member are configured in such a manner that at least a portion of a culture solution flowing through the first flow path is supplied to the first accommodation section;
further wherein the hydrogel is selected from the group consisting of: an agarose gel, a polyacrylamide gel, a sodium alginate, and a collagen gel.

2. The fluidic chip according to claim 1, wherein
the base or the lid member has a first inlet and a first outlet, and
the first flow path is provided in such a manner that the culture solution injected through the first inlet flows through the first flow path and is discharged through the first outlet.

3. The fluidic chip according to claim 1, further wherein
the base and the lid member are configured to define a second flow path when the lid member is joined to the base,
the base or the lid member has a second inlet and a second outlet,
the second flow path is provided in such a manner that a culture solution or a normal saline solution injected through the second inlet flows through the second flow path and is discharged through the second outlet, and the base and the lid member are configured in such a manner that at least a portion of the culture solution flowing through the first flow path and a portion of the culture solution or the normal saline solution flowing through the second flow path are both supplied to the first accommodation section.

4. The fluidic chip according to claim 1, further comprising the first culture vessel accommodated in the first accommodation section, wherein the lid member is configured to serve as a flow path ceiling of the first flow path and/or a ceiling of the accommodation section.

5. The fluidic chip according to claim 1, wherein the porous body is made of a material selected from at least one of a porous material sheet, a mesh, an etching sheet, a non-woven fabric, and a woven fabric.

6. The fluidic chip according to claim 1, further wherein the base and the lid member are configured to define a second accommodation section for attachably/detachably accommodating a second culture vessel when the lid member is joined to the base, wherein the second culture vessel comprises a culture gel having cells or a cell tissue embedded in the culture gel and includes a light-permeable window made from a hydrogel or a porous body, and the base and the lid member are configured in such a manner that the culture solution flowing through the first flow path permeates into and is supplied to an inside of the first culture vessel accommodated in the first accommodation section, and that the culture solution which has flowed inside the first culture vessel as osmotic flow permeates into and is supplied to an inside of the second culture vessel accommodated in the second accommodation section.

7. The fluidic chip according to claim 6, further comprising the first culture vessel accommodated in the first accommodation section, wherein the first culture vessel comprises a first frame that has a polyhedral shape having a plurality of openings in respective faces, a first window provided in at least one of the plurality of openings, and a culture gel including embedded cells or a cell tissue held within the first culture vessel, the first window is made from a light-permeable hydrogel or a porous body, the first accommodation section has a first inflow port for inflow of the culture solution and a first outflow port for outflow of the culture solution, the plurality of openings of the first frame includes first and second openings in which the first windows are not provided, and the first accommodation section and the first culture vessel are configured in such a manner that the first opening of the first frame lies adjacent to the first inflow port, and that the second opening of the first frame lies adjacent to the first outflow port.

8. The fluidic chip according to claim 6, further comprising the second culture vessel accommodated in the second accommodation section, wherein the second culture vessel comprises a second frame that has a polyhedral shape having a plurality of openings in respective faces, a second window provided in at least one of the plurality of openings, and a culture gel including embedded cells or a cell tissue enclosed within the second culture vessel, the second window is made from a light-permeable hydrogel or a porous body, the second accommodation section has a second inflow port for inflow of the culture solution and a second outflow port for outflow of the culture solution, the plurality of openings of the second frame includes third and fourth openings in which the second windows are not provided, and the second accommodation section and the second culture vessel are configured in such a manner that the third opening of the second frame lies adjacent to the second inflow port, and that the fourth opening of the second frame lies adjacent to the second outflow port.

9. The fluidic chip according to claim 6, further wherein the base and the lid member are configured to define a third accommodation section for attachably/detachably accommodating a third culture vessel when the lid member is joined to the base, the third culture vessel includes a light-permeable window made from a hydrogel or a porous body, and the base and the lid member are configured in such a manner that the culture solution flowing through the first flow path permeates into and is supplied to the inside of the first culture vessel accommodated in the first accommodation section, and that the culture solution which has flowed inside the first culture vessel as osmotic flow permeates into and is supplied to the inside of the second culture vessel accommodated in the second accommodation section and to the inside of the third culture vessel accommodated in the third accommodation section.

10. The fluidic chip according to claim 9, wherein the third culture vessel comprises a culture gel including embedded cells or a cell tissue.

11. A fluidic chip for cell culture use, comprising a base, wherein the base has a first flow path and a first accommodation section for attachably/detachably accommodating a first culture vessel, the first culture vessel encloses a culture gel having cells or a cell tissue embedded in the culture gel and includes a light-permeable window made from a hydrogel or a porous body, wherein the light-permeable window made from the hydrogel has a gel strength of from about 50 g/cm$^2$ to about 10000 g/cm$^2$, the first accommodation section has a socket with which the first culture vessel is engageable, and the base is configured in such a manner that at least a portion of a culture solution flowing through the first flow path is supplied to the first accommodation section;

further wherein the hydrogel is selected from the group consisting of: an agarose gel, a polyacrylamide gel, a sodium alginate, and a collagen gel.

* * * * *